US012575763B2

(12) United States Patent
Budiman et al.

(10) Patent No.: US 12,575,763 B2
(45) Date of Patent: Mar. 17, 2026

(54) SYSTEMS, DEVICES, AND METHODS WITH DURATION-BASED ADJUSTMENT OF SENSOR DATA

(71) Applicant: ABBOTT DIABETES CARE INC., Alameda, CA (US)

(72) Inventors: Erwin S. Budiman, Fremont, CA (US); Claire Bhogal, Witney (GB); Steven Scott, Pleasanton, CA (US); Marc B. Taub, Mountain View, CA (US)

(73) Assignee: ABBOTT DIABETES CARE INC., Alameda, CA (US)

( * ) Notice: Subject to any disclaimer, the term of this patent is extended or adjusted under 35 U.S.C. 154(b) by 938 days.

(21) Appl. No.: 17/704,824

(22) Filed: Mar. 25, 2022

(65) Prior Publication Data

US 2022/0211307 A1 Jul. 7, 2022

Related U.S. Application Data

(63) Continuation of application No. 16/204,358, filed on Nov. 29, 2018, now Pat. No. 12,310,722, which is a (Continued)

(51) Int. Cl.
*A61B 5/145* (2006.01)
*A61B 5/00* (2006.01)
(Continued)

(52) U.S. Cl.
CPC ........ *A61B 5/14532* (2013.01); *A61B 5/0022* (2013.01); *A61B 5/076* (2013.01);
(Continued)

(58) Field of Classification Search
CPC ...... G16H 40/40; A61B 5/1495; A61B 5/145; A61B 5/0022; A61B 5/14503; A61B 2560/0223
See application file for complete search history.

(56) References Cited

U.S. PATENT DOCUMENTS 4,592,745 A 6/1986 Rex et al.
4,627,445 A 12/1986 Garcia et al.
(Continued)

FOREIGN PATENT DOCUMENTS

CA 2 766 693 9/2011
CA 2 766 685 12/2011
(Continued)

OTHER PUBLICATIONS

U.S. Appl. No. 16/204,358 (2019/0117138), filed Nov. 29, 2018 (Apr. 25, 2019).
(Continued)

*Primary Examiner* — Christian Jang
(74) *Attorney, Agent, or Firm* — ONE LLP

(57) ABSTRACT

Embodiments that compensate for changes to sensor response characteristics (e.g., sensitivity) due to time durations are disclosed. The time durations can be the amount of time the sensor is in a post-manufacture packaged state prior to use, or the amount of time the sensor is in use. Sensor response changes due to other variables can also be compensated for.

28 Claims, 5 Drawing Sheets

Sensor data is collected with the analyte sensor at least partially inserted into a human body /402

The sensor data is adjusted to compensate for sensor response change due to the shelf duration /404

An analyte level representative of the adjusted sensor data can be output /406

400

Related U.S. Application Data continuation of application No. PCT/US2018/030619, filed on May 2, 2018.

(60) Provisional application No. 62/624,665, filed on Jan. 31, 2018, provisional application No. 62/500,955, filed on May 3, 2017.

(51) Int. Cl.
| | | |
|---|---|---|
| *A61B 5/07* | (2006.01) | |
| *A61B 5/1495* | (2006.01) | |
| *G16H 40/40* | (2018.01) | |

(52) U.S. Cl.
CPC .......... *A61B 5/145* (2013.01); *A61B 5/14503* (2013.01); *A61B 5/1495* (2013.01); *A61B 5/6833* (2013.01); *A61B 5/6849* (2013.01); *G16H 40/40* (2018.01); *A61B 2560/0223* (2013.01)

(56) References Cited

U.S. PATENT DOCUMENTS

| | | | |
|---|---|---|---|
| 4,650,547 | A | 3/1987 | Gough |
| 4,703,756 | A | 11/1987 | Gough et al. |
| 4,750,496 | A | 6/1988 | Reinhart et al. |
| 4,924,879 | A | 5/1990 | O'Brien |
| 5,034,112 | A | 7/1991 | Murase et al. |
| 5,089,112 | A | 2/1992 | Skotheim et al. |
| 5,145,381 | A | 9/1992 | Volz |
| 5,264,103 | A | 11/1993 | Yoshioka et al. |
| 5,267,963 | A | 12/1993 | Bachynsky |
| 5,318,583 | A | 6/1994 | Rabenau et al. |
| 5,352,351 | A | 10/1994 | White et al. |
| 5,390,671 | A | 2/1995 | Lord et al. |
| 5,391,250 | A | 2/1995 | Cheney et al. |
| 5,407,431 | A | 4/1995 | Botich et al. |
| 5,411,647 | A | 5/1995 | Johnson et al. |
| 5,497,772 | A | 3/1996 | Schulman et al. |
| 5,584,813 | A | 12/1996 | Livingston et al. |
| 5,626,566 | A | 5/1997 | Petersen et al. |
| 5,695,623 | A | 12/1997 | Michel et al. |
| 5,786,439 | A | 7/1998 | Van Antwerp et al. |
| 5,791,344 | A | 8/1998 | Schulman et al. |
| 5,863,400 | A | 1/1999 | Drummond et al. |
| 5,865,804 | A | 2/1999 | Bachynsky |
| 5,954,643 | A | 9/1999 | VanAntwerp et al. |
| 5,971,941 | A | 10/1999 | Simons et al. |
| 6,001,067 | A | 12/1999 | Shults et al. |
| 6,093,172 | A | 7/2000 | Funderburk et al. |
| 6,103,033 | A | 8/2000 | Say et al. |
| 6,106,484 | A | 8/2000 | Terwilliger et al. |
| 6,149,626 | A | 11/2000 | Bachynsky et al. |
| 6,168,957 | B1 | 1/2001 | Matzinger et al. |
| 6,175,752 | B1 | 1/2001 | Say et al. |
| 6,212,417 | B1 | 4/2001 | Ikeda et al. |
| 6,237,394 | B1 | 5/2001 | Harris et al. |
| 6,259,181 | B1 | 7/2001 | Kawano et al. |
| 6,275,717 | B1 | 8/2001 | Gross et al. |
| 6,283,982 | B1 | 9/2001 | Levaughn et al. |
| 6,293,924 | B1 | 9/2001 | Safabash et al. |
| 6,293,925 | B1 | 9/2001 | Safabash et al. |
| 6,360,888 | B1 | 3/2002 | McIvor et al. |
| 6,366,794 | B1 | 4/2002 | Moussy et al. |
| 6,368,141 | B1 | 4/2002 | VanAntwerp et al. |
| 6,377,829 | B1 | 4/2002 | Al-Ali |
| 6,400,974 | B1 | 6/2002 | Lesho |
| 6,424,847 | B1 | 7/2002 | Mastrototaro et al. |
| 6,475,372 | B1 | 11/2002 | Ohara et al. |
| 6,475,750 | B1 | 11/2002 | Han et al. |
| 6,522,903 | B1 | 2/2003 | Berman et al. |
| 6,558,321 | B1 | 5/2003 | Burd et al. |
| 6,560,471 | B1 | 5/2003 | Heller et al. |
| 6,565,509 | B1 | 5/2003 | Say et al. |
| 6,579,690 | B1 | 6/2003 | Bonnecaze et al. |
| 6,587,704 | B1 | 7/2003 | Fine et al. |
| 6,607,543 | B2 | 8/2003 | Purcell et al. |
| 6,637,611 | B2 | 10/2003 | Luch |
| 6,695,860 | B1 | 2/2004 | Ward et al. |
| 6,809,653 | B1 | 10/2004 | Mann et al. |
| 6,835,553 | B2 | 12/2004 | Han et al. |
| 6,850,859 | B1 | 2/2005 | Schuh |
| 6,931,327 | B2 | 8/2005 | Good, Jr. et al. |
| 6,950,028 | B2 | 9/2005 | Zweig |
| 6,960,192 | B1 | 11/2005 | Flaherty et al. |
| 6,990,366 | B2 | 1/2006 | Say et al. |
| 7,027,859 | B1 | 4/2006 | McNichols et al. |
| 7,110,803 | B2 | 9/2006 | Shults et al. |
| 7,144,384 | B2 | 12/2006 | Gorman et al. |
| 7,207,974 | B2 | 4/2007 | Safabash et al. |
| 7,220,387 | B2 | 5/2007 | Flaherty et al. |
| 7,299,082 | B2 | 11/2007 | Feldman et al. |
| 7,344,500 | B2 | 3/2008 | Talbot et al. |
| 7,381,184 | B2 | 6/2008 | Funderburk et al. |
| 7,481,819 | B2 | 1/2009 | Koeppel et al. |
| 7,491,303 | B2 | 2/2009 | Sakata et al. |
| 7,585,287 | B2 | 9/2009 | Bresina et al. |
| 7,643,798 | B2 | 1/2010 | Ljung |
| 7,699,807 | B2 | 4/2010 | Faust et al. |
| 7,731,691 | B2 | 6/2010 | Cote et al. |
| 7,837,633 | B2 | 11/2010 | Conway et al. |
| 7,846,132 | B2 | 12/2010 | Gravesen et al. |
| 7,867,244 | B2 | 1/2011 | Lathrop et al. |
| 7,883,473 | B2 | 2/2011 | LeVaughn et al. |
| 7,946,984 | B2 | 5/2011 | Brister et al. |
| 8,016,774 | B2 | 9/2011 | Freeman et al. |
| 8,028,837 | B2 | 10/2011 | Gerstle et al. |
| 8,175,673 | B2 | 5/2012 | Say et al. |
| 8,221,332 | B2 | 7/2012 | Robbins et al. |
| 8,382,681 | B2 | 2/2013 | Escutia et al. |
| 8,396,670 | B2 | 3/2013 | St-Pierre |
| 8,398,664 | B2 | 3/2013 | Lamps et al. |
| 8,469,986 | B2 | 6/2013 | Schraga |
| 8,515,519 | B2 | 8/2013 | Brister et al. |
| 8,747,363 | B2 | 6/2014 | Nielsen et al. |
| 8,750,955 | B2 | 6/2014 | Brister et al. |
| 8,945,056 | B2 | 2/2015 | Iio et al. |
| 9,241,631 | B2 | 1/2016 | Valdes et al. |
| 9,402,544 | B2 | 8/2016 | Yee et al. |
| 9,474,479 | B2 | 10/2016 | Pusey et al. |
| 9,504,471 | B2 | 11/2016 | Vaitekunas et al. |
| 9,566,384 | B2 | 2/2017 | Gyrn et al. |
| 9,668,682 | B2 | 6/2017 | Brister et al. |
| 9,808,574 | B2 | 11/2017 | Yodfat et al. |
| 10,292,632 | B2 | 5/2019 | Lee et al. |
| 10,772,547 | B1 | 9/2020 | Lee et al. |
| 10,820,842 | B2 | 11/2020 | Harper |
| 10,827,954 | B2 | 11/2020 | Hoss et al. |
| 10,874,338 | B2 | 12/2020 | Stafford |
| 10,881,341 | B1 | 1/2021 | Curry et al. |
| 10,945,647 | B2 | 3/2021 | Mazza et al. |
| 10,945,649 | B2 | 3/2021 | Lee et al. |
| 10,952,653 | B2 | 3/2021 | Harper |
| 10,959,654 | B2 | 3/2021 | Curry et al. |
| 10,966,644 | B2 | 4/2021 | Stafford |
| 10,973,443 | B2 | 4/2021 | Funderburk et al. |
| 10,980,461 | B2 | 4/2021 | Simpson et al. |
| 11,000,213 | B2 | 5/2021 | Kamath et al. |
| 11,000,216 | B2 | 5/2021 | Curry et al. |
| 11,013,440 | B2 | 5/2021 | Lee et al. |
| 11,020,031 | B1 | 6/2021 | Simpson et al. |
| 11,064,917 | B2 | 7/2021 | Simpson et al. |
| 11,141,084 | B2 | 10/2021 | Funderburk et al. |
| 11,202,591 | B2 | 12/2021 | Yee et al. |
| 11,298,056 | B2 | 4/2022 | Harper |
| 2002/0010390 | A1 | 1/2002 | Guice et al. |
| 2002/0022855 | A1 | 2/2002 | Bobroff et al. |
| 2002/0043651 | A1 | 4/2002 | Darrow et al. |
| 2002/0161288 | A1 | 10/2002 | Shin et al. |
| 2002/0169439 | A1 | 11/2002 | Flaherty |
| 2002/0177764 | A1 | 11/2002 | Sohrab |
| 2003/0003524 | A1 | 1/2003 | Taniike et al. |
| 2003/0028184 | A1 | 2/2003 | Lebel et al. |
| 2003/0076082 | A1 | 4/2003 | Morgan et al. |

(56) References Cited

U.S. PATENT DOCUMENTS

| | | |
|---|---|---|
| 2003/0100821 A1 | 5/2003 | Heller et al. |
| 2003/0225373 A1 | 12/2003 | Bobroff et al. |
| 2004/0002682 A1 | 1/2004 | Kovelman et al. |
| 2004/0010207 A1 | 1/2004 | Flaherty et al. |
| 2004/0018486 A1 | 1/2004 | Dunn et al. |
| 2004/0022438 A1 | 2/2004 | Hibbard |
| 2004/0106858 A1 | 6/2004 | Say et al. |
| 2004/0127777 A1 | 7/2004 | Ruchti et al. |
| 2004/0133164 A1 | 7/2004 | Funderburk et al. |
| 2004/0186365 A1 | 9/2004 | Jin et al. |
| 2004/0204673 A1 | 10/2004 | Flaherty |
| 2004/0204687 A1 | 10/2004 | Mogensen et al. |
| 2004/0244151 A1 | 12/2004 | Sakata et al. |
| 2005/0004439 A1 | 1/2005 | Shin et al. |
| 2005/0027180 A1 | 2/2005 | Goode, Jr. et al. |
| 2005/0027463 A1 | 2/2005 | Goode, Jr. et al. |
| 2005/0038332 A1 | 2/2005 | Saidara et al. |
| 2005/0038465 A1 | 2/2005 | Shraga |
| 2005/0043598 A1 | 2/2005 | Goode, Jr. et al. |
| 2005/0059871 A1 | 3/2005 | Gough et al. |
| 2005/0069892 A1 | 3/2005 | Iyengar et al. |
| 2005/0101932 A1 | 5/2005 | Cote et al. |
| 2005/0143636 A1 | 6/2005 | Zhang et al. |
| 2005/0151976 A1 | 7/2005 | Toma |
| 2005/0215871 A1 | 9/2005 | Feldman et al. |
| 2005/0239154 A1 | 10/2005 | Feldman et al. |
| 2005/0245799 A1 | 11/2005 | Brauker et al. |
| 2005/0283114 A1 | 12/2005 | Bresina et al. |
| 2005/0283208 A1 | 12/2005 | Von Arx et al. |
| 2006/0019327 A1 | 1/2006 | Brister et al. |
| 2006/0020187 A1 | 1/2006 | Brister et al. |
| 2006/0020189 A1 | 1/2006 | Brister et al. |
| 2006/0020192 A1 | 1/2006 | Brister et al. |
| 2006/0036143 A1 | 2/2006 | Brister et al. |
| 2006/0081469 A1 | 4/2006 | Lee |
| 2006/0094944 A1 | 5/2006 | Chuang |
| 2006/0094945 A1 | 5/2006 | Barman et al. |
| 2006/0095014 A1 | 5/2006 | Ethelfeld |
| 2006/0142651 A1 | 6/2006 | Brister et al. |
| 2006/0155180 A1 | 7/2006 | Brister et al. |
| 2006/0222566 A1 | 10/2006 | Brauker et al. |
| 2006/0229512 A1 | 10/2006 | Petisce et al. |
| 2006/0258929 A1 | 11/2006 | Goode, Jr. et al. |
| 2006/0258959 A1 | 11/2006 | Sode |
| 2006/0281985 A1 | 12/2006 | Ward et al. |
| 2006/0293576 A1 | 12/2006 | Van Antwerp et al. |
| 2007/0016129 A1 | 1/2007 | Liniger et al. |
| 2007/0027381 A1 | 2/2007 | Stafford |
| 2007/0032706 A1 | 2/2007 | Kamath et al. |
| 2007/0038044 A1 | 2/2007 | Dobbles et al. |
| 2007/0060801 A1 | 3/2007 | Neinast |
| 2007/0073129 A1 | 3/2007 | Shah et al. |
| 2007/0093754 A1 | 4/2007 | Mogensen et al. |
| 2007/0135774 A1 | 6/2007 | Turner et al. |
| 2007/0142727 A1 | 6/2007 | Zhang et al. |
| 2007/0173710 A1 | 7/2007 | Petisce et al. |
| 2007/0208244 A1 | 9/2007 | Brauker et al. |
| 2007/0219480 A1 | 9/2007 | Kamen et al. |
| 2007/0249922 A1 | 10/2007 | Peyser et al. |
| 2007/0255116 A1 | 11/2007 | Mehta et al. |
| 2007/0299617 A1 | 12/2007 | Willis |
| 2008/0009692 A1 | 1/2008 | Stafford |
| 2008/0009805 A1 | 1/2008 | Ethefeld |
| 2008/0097246 A1 | 4/2008 | Stafford |
| 2008/0114280 A1 | 5/2008 | Stafford |
| 2008/0129486 A1 | 6/2008 | Jeckelmann et al. |
| 2008/0172205 A1 | 7/2008 | Breton et al. |
| 2008/0242962 A1 | 10/2008 | Roesicke et al. |
| 2008/0255440 A1 | 10/2008 | Eilersen et al. |
| 2008/0269687 A1 | 10/2008 | Chong et al. |
| 2008/0275313 A1 | 11/2008 | Brister et al. |
| 2008/0278333 A1 | 11/2008 | Fennell et al. |
| 2008/0281179 A1 | 11/2008 | Fennell et al. |
| 2008/0300476 A1 | 12/2008 | Stafford |
| 2008/0312842 A1 | 12/2008 | Hayter et al. |
| 2008/0319414 A1 | 12/2008 | Yodfat et al. |
| 2009/0054737 A1 | 2/2009 | Magar et al. |
| 2009/0076360 A1 | 3/2009 | Brister et al. |
| 2009/0099521 A1 | 4/2009 | Gravesen et al. |
| 2009/0102678 A1 | 4/2009 | Mazza et al. |
| 2009/0124979 A1 | 5/2009 | Raymond et al. |
| 2009/0143659 A1 | 6/2009 | Li et al. |
| 2009/0163789 A1 | 6/2009 | Say et al. |
| 2009/0178459 A1 | 7/2009 | Li et al. |
| 2009/0198186 A1 | 8/2009 | Mernoe et al. |
| 2009/0216215 A1 | 8/2009 | Thalmann et al. |
| 2009/0240121 A1 | 9/2009 | Bickoff |
| 2009/0247857 A1 | 10/2009 | Harper et al. |
| 2009/0291634 A1 | 11/2009 | Saarisalo |
| 2010/0045425 A1 | 2/2010 | Chivallier |
| 2010/0057042 A1 | 3/2010 | Hayter |
| 2010/0094111 A1 | 4/2010 | Heller et al. |
| 2010/0145377 A1 | 6/2010 | Lai et al. |
| 2010/0160759 A1 | 6/2010 | Celentano et al. |
| 2010/0198034 A1 | 8/2010 | Thomas et al. |
| 2010/0230285 A1 | 9/2010 | Hoss et al. |
| 2010/0274515 A1 | 10/2010 | Hoss et al. |
| 2011/0021889 A1 | 1/2011 | Hoss et al. |
| 2011/0058485 A1 | 3/2011 | Sloan |
| 2011/0178378 A1 | 7/2011 | Mernoe et al. |
| 2011/0193704 A1 | 8/2011 | Harper et al. |
| 2011/0210830 A1 | 9/2011 | Talty et al. |
| 2011/0213225 A1 | 9/2011 | Bernstein et al. |
| 2011/0319729 A1 | 12/2011 | Donnay et al. |
| 2011/0320130 A1 | 12/2011 | Valdes et al. |
| 2012/0003933 A1 | 1/2012 | Baker et al. |
| 2012/0078071 A1 | 3/2012 | Bohm et al. |
| 2012/0084053 A1 | 4/2012 | Yuen et al. |
| 2012/0233679 A1 | 9/2012 | Shedrinsky |
| 2012/0238851 A1 | 9/2012 | Kamen et al. |
| 2012/0255875 A1 | 10/2012 | Vicente et al. |
| 2012/0265037 A1* | 10/2012 | Bohm ............... A61B 5/14503 |
| | | 600/309 |
| 2012/0309302 A1 | 12/2012 | Buhot |
| 2014/0188402 A1 | 7/2014 | Garcia et al. |
| 2015/0005601 A1 | 1/2015 | Hoss et al. |
| 2015/0018639 A1 | 1/2015 | Stafford |
| 2015/0025345 A1 | 1/2015 | Funderburk et al. |
| 2015/0173661 A1 | 6/2015 | Myles |
| 2017/0074757 A1 | 3/2017 | Garcia et al. |
| 2017/0112531 A1 | 4/2017 | Schoonmaker et al. |
| 2019/0274598 A1 | 9/2019 | Scott et al. |

FOREIGN PATENT DOCUMENTS

| | | |
|---|---|---|
| DE | 20 2015 010 002 U1 | 12/2022 |
| EP | 1 391 728 | 2/2004 |
| EP | 1 413 879 | 1/2012 |
| EP | 2 498 196 | 9/2012 |
| EP | 3 575 796 | 12/2019 |
| EP | 3730045 | 3/2022 |
| EP | 1789116 | 5/2023 |
| WO | WO 97/18639 | 5/1997 |
| WO | WO 00/49941 | 8/2000 |
| WO | WO 2001/17875 | 3/2001 |
| WO | WO 02/058537 | 8/2002 |
| WO | WO 2002/058537 | 8/2002 |
| WO | WO 03/012422 | 2/2003 |
| WO | WO 03/026728 | 4/2003 |
| WO | WO 03/032411 | 4/2003 |
| WO | WO 03/094714 | 11/2003 |
| WO | WO 2004/006982 | 1/2004 |
| WO | WO 2004/098682 | 11/2004 |
| WO | WO 2005/011489 | 2/2005 |
| WO | WO 2005/011779 | 2/2005 |
| WO | WO 2005/046780 | 5/2005 |
| WO | WO 2005/070287 | 8/2005 |
| WO | WO 2006/026741 | 3/2006 |
| WO | WO 2006/121921 | 11/2006 |
| WO | WO 2008/021913 | 2/2008 |
| WO | WO 2008/073813 | 6/2008 |
| WO | WO 2008/114223 | 9/2008 |
| WO | WO 2008/115409 | 9/2008 |
| WO | WO 2008/155377 | 12/2008 |

(56)　　　　　References Cited

FOREIGN PATENT DOCUMENTS

| WO | WO 2008/157821 | 12/2008 |
| WO | WO 2009/001347 | 12/2008 |
| WO | WO 2009/007287 | 1/2009 |
| WO | WO 2009/035773 | 3/2009 |
| WO | WO 2009/039013 | 3/2009 |
| WO | WO 2009/066288 | 3/2009 |
| WO | WO 2010/099507 | 9/2010 |
| WO | WO 2011/011643 | 1/2011 |
| WO | WO 2012/142502 | 10/2012 |
| WO | WO 2013/019225 | 2/2013 |
| WO | WO 2013/090791 | 6/2013 |

OTHER PUBLICATIONS

U.S. Appl. No. 16/204,358, filed May 20, 2022 Advisory Action.
U.S. Appl. No. 16/204,358, filed May 17, 2022 Response after Final Office Action.
U.S. Appl. No. 16/204,358, filed Mar. 22, 2022 Final Office Action.
U.S. Appl. No. 16/204,358, filed Dec. 27, 2021 Response after Non-Final Office Action.
U.S. Appl. No. 16/204,358, filed Sep. 24, 2021 Non-Final Office Action.
U.S. Appl. No. 16/204,358, filed Aug. 25, 2021 Response to Restriction Requirement.
U.S. Appl. No. 16/204,358, filed Jun. 25, 2021 Restriction Requirement.
WO PCT/US2018/030619 ISR and Written Opinion Jun. 26, 2018.
Hoss, U., et al., "Factory-Calibrated Continuous Glucose Sensors: The Science Behind the Technology", Diabetes Technology & Therapeutics, 2017, vol. 19, No. S2, pp. 5-44-5-50.
Pavelkova, A., "Time Temperature Indicators as Devices Intelligent Packaging," Acta Universitatis Agriculturae et Silviculturae Mendelianae Brunensis, 2013, vol. LXI, No. 1, pp. 245-251.
U.S. Appl. No. 61/227,967, filed Jul. 23, 2009, Hoss, et al.
"Blood glucose monitoring" retrieved from "https://web.archive.org/web/20111215063153/http://en.wikipedia.org/wiki/Blood_glucose_monitoring" on Aug. 1, 2021, 6 pages.
"In Vivo Glucose Sensing", Chemical Analysis, A Series of Monographs on Analytical Chemistry and its Applications, vol. 174, 466 pages (2010).
"In Vivo Glucose Sensing", Chemical Analysis, A Series of Monographs on Analytical Chemistry and its Applications, vol. 174, 62 pages (2010).
"Near field communication" retrieved from "http://en.wikipedia.org/w/index.php?title=Near_field_communication&oldid=543740757" on Jun. 27, 2014, 14 pages.
Alcock, et al., "Continuous Analyte Monitoring to Aid Clinical Practice", IEEE Engineering in Medicine and Biology, pp. 319-325 (1994).
Bard, et al., Electrochemical Methods, Fundamentals and Applications, pp. 174-175 (1980).
Bequette, "Continuous Glucose Monitoring: Real Time Algorithms for Calibration, Filtering, and Alarms", Journal of Diabetes Science and Technology, 4(2):404-418 (2010).
Cengiz, et al., "A Tale of Two Compartments: Interstitial Versus Blood Glucose Monitoring", Diabetes Technology & Therapeutics, 11(1):S-11-S16 (2009).
Chen, et al., "Defining the Period of Recovery of the Glucose Concentration after Its Local Perturbation by the Implantation of a Miniature Sensor", Clin Chem Lab Med, 40(8):786-789 (2002).
Chen, et al., "Glucose microbiosensor based on alumina sol gel matrix/eletropolymerized composite membrane", Biosensors and Bioelectronics, 17:1005-1013 (2002).
Chen, et al., "In Situ Assembled Mass-Transport Controlling Micromembranes and Their Application in Implanted Amperometric Glucose Sensors", Analytical Chemistry, 72(16):3757-3763 (2000).
Chen, et al., "In vivo Glucose Monitoring with Miniature "Wired" Glucose Oxidase Electrodes", Analytical Sciences, 17:i297-i300 (2001).
Choleau, et al., "Calibration of a subcutaneous amperometric glucose sensor Part 1. Effect of measurement uncertainties on the determination of sensor sensitivity and background current", Biosensors and Bioelectronics, 17:641-646 (2002).
Chung, "In vitro Evaluation of the Continuous Monitoring Glucose Sensors with Perfluorinated Tetrafluoroethylene Coatings", Bull. Korean Chem. Soc., 24(4):514-516 (2003).
Csöregi, et al., "Design, Characterization, and One-Point in Vivo Calibration of a Subcutaneously Implanted Glucose Electrode", Anal. Chem., 66(19):3131-3138 (1994).
De Block, et al., "Minimally-Invasive and Non-Invasive Continuous Glucose Monitoring Systems: Indications, Advantages, Limitations and Clinical Aspects", Current Diabetes Reviews, 4:159-168 (2008).
Decuir, "Bluetooth 4.0:Low Energy", Standards Architect, CSR Technology, Councilor, Bluetooth Architecture Review Board, IEEE Region 6 Northwest Area Chair, 104 pages (2012).
Dementyev, et al., "Power Consumption Analysis of Bluetooth Low Energy, ZigBee and ANT Sensor Nodes in a Cyclic Sleep Scenario", IEEE International Wireless Symposium (IWS), 5 pages (2013).
DexCom™ STS™ Continuous Glucose Monitoring System, User's Guide, DexCom, Inc., 57 pages (2006).
Facchinetti, et al., "Enhanced Accuracy of Continuous Glucose Monitoring by Online Extended Kalman Filtering", Diabetes Technology & Therapeutics, 12(5):353-363 (2010).
Feldman, et al., "A Continuous Glucose Sensor Based on Wired Enzyme™ Technology—Results from a 3-Day Trial in Patients with Type 1 Diabetes", Diabetes Technology & Therapeutics, 5(5):769-779 (2003).
Fischer, "Fundamentals of Glucose Sensors", Diabetic Medicine, 8:309-321 (1991).
FreeStyle Navigator Continuous Glucose Monitoring System, Summary of Safety and Effectiveness Data in support of Pre-Market Approval (PMA) No. P050020, Abbott Diabetes Care, 27 pages (2008).
FreeStyle Navigator Continuous Glucose Monitoring System, User Guide, Abbott Diabetes Care Inc., 195 pages (2008).
Gerritsen, et al., "Subcutaneously implantable glucose sensors in patients with diabetes mellitus; still many problems", Dutch Journal of Medicine, 146(28):1313-1316 (2002) (with English Machine Translation).
Guardian® Real-Time, Continuous Glucose Monitoring System, User Guide, Medtronic MiniMed, Inc., 181 pages (2006).
Guardian® RT, Continuous Glucose Monitoring System, REF MMT-7900, User Guide, Medtronic MiniMed, 128 pages (2005).
Heinemann, "Continuous Glucose Monitoring by Means of the Microdialysis Technique: Underlying Fundamental Aspects", Diabetes Technology & Therapeutics, 5(4):545-561 (2003).
Heise, et al., "Hypoglycemia Warning Signal and Glucose Sensors: Requirements and Concepts", Diabetes Technology & Therapeutics, 5(4):563-571 (2003).
Heller, "Implanted Electrochemical Glucose Sensors for the Management of Diabetes", Annu. Rev. Biomed. Eng., 01:153-175 (1999).
Heller, et al., "Electrochemical Glucose Sensors and Their Applications in Diabetes Management", Chemical Reviews, 108(7):2482-2505 (2008).
Jiménez, et al., "Glucose sensor based on an amperometric microelectrode with a photopolymerizable enzyme membrane", Sensors and Actuators B, 26-27:421-424 (1995).
Johnson, et al., "Reduction of Electrooxidizable Interferent Effects: Optimization of the Applied Potential for Amperometric Glucose Sensors", Electroanalysis, 6:321-326 (1994).
Klonoff, "A Review of Continuous Glucose Monitoring Technology", Diabetes Technology & Therapeutics, 7(5):770-775 (2005).
Klonoff, "Continuous Glucose Monitoring: Roadmap for 21st century diabetes therapy", Diabetes Care, 28(5):1231-1239 (2005).
Knobbe, et al., "The Extended Kalman Filter for Continuous Glucose Monitoring", Diabetes Technology & Therapeutics, 7(1):15-27 (2005).
Koudelka, et al., "In-vivo Behaviour of Hypodermically Implanted Microfabricated Glucose Sensors", Biosensors & Bioelectronics, 6:31-36 (1991).

(56)                References Cited

OTHER PUBLICATIONS

Koudelka-Hep, "Electrochemical Sensors for in vivo Glucose Sensing", Biosensors in the Body: Continuous in vivo Monitoring, pp. 57-77 (1997).

Kuure-Kinsey, et al., "A Dual-Rate Kalman Filter for Continuous Glucose Monitoring", Proceedings of the 28th IEEE, EMBS Annual International Conference, pp. 63-66 (2006).

Kvist, et al., "Recent Advances in Continuous Glucose Monitoring: Biocompatibility of Glucose Sensors for Implantation in Subcutis", Journal of Diabetes Science and Technology, 1(5):746-752 (2007).

Lodwig, et al., "Continuous Glucose Monitoring with Glucose Sensors: Calibration and Assessment Criteria", Diabetes Technology & Therapeutics, 5(4):573-587 (2003).

Ming Li, et al., "Implantable Electrochemical Sensors for Biomedical and Clinical Applications: Progress, Problems, and Future Possibilities", Current Medicinal Chemistry, 14:937-951 (2007).

Moatti-Sirat, et al., "Evaluating in vitro and in vivo the interference of ascorbate and acetaminophen on glucose detection by a needle-type glucose sensor", Biosensors and Bioelectronics, 7(5):345-352 (1992).

Morak, et al., "Design and Evaluation of a Telemonitoring Concept Based on NFC-Enabled Mobile Phones and Sensor Devices", IEEE Transactions on Information Technology in Biomedicine, 16(1):17-23 (2012).

Movassaghi, et al., "Wireless Technologies for Body Area Networks: Characteristics and Challenges", IEEE, International Symposium on Communications and Information Technologies (ISCIT), pp. 42-47 (2012).

Nishida, et al., "Development of a ferrocene-mediated needle-type glucose sensor covered with newly designed biocompatible membrane, 2-methacryloyloxyethyl phosphorylcholine-co-n-butyl methacrylate", Medical Progress through Technology, 21:91-103 (1995).

Onuki, et al., "A Review of the Biocompatibility of Implantable Devices: Current Challenges to Overcome Foreign Body Response", Journal of Diabetes Science and Technology, 2(6):1003-1015 (2008).

Palerm, et al., "Hypoglycemia Prediction and Detection Using Optimal Estimation", Diabetes Technology & Therapeutics, 7(1):3-14 (2005).

Poitout, et al., "Calibration in dogs of a subcutaneous miniaturized glucose sensor using a glucose meter for blood glucose determination", Biosensors & Bioelectronics, 7:587-592 (1992).

Rebrin, et al., "Subcutaneous glucose predicts plasma glucose independent of insulin: implications for continuous monitoring", American Journal of Physiology-Endocrinology and Metabolism, 277(3):E561-E571 (1999).

Renard, "Implantable glucose sensors for diabetes monitoring", Min Invas Ther & Allied Technol, 13(2):78-86 (2004).

Rhodes, et al., "Prediction of Pocket-Portable and Implantable Glucose Enzyme Electrode Performance from Combined Species Permeability and Digital Simulation Analysis", Analytical Chemistry, 66(9):1520-1529 (1994).

Robert, "Continuous Monitoring of Blood Glucose", Horm Res 57(suppl 1):81-84 (2002).

Schlosser, et al., "Biocompatibility of Active Implantable Devices", Biosensors in the Body: Continuous in vivo Monitoring, pp. 139-170 (1997).

Schmidt, et al., "Calibration of a wearable glucose sensor", The International Journal of Artificial Organs, 15(1):55-61 (1992).

Schmidtke, et al., "Accuracy of the One-Point in Vivo Calibration of "Wired" Glucose Oxidase Electrodes Implanted in Jugular Veins of Rats in Periods of Rapid Rise and Decline of the Glucose Concentration", Anal. Chem., 70:2149-2155 (1998).

Specification of the Bluetooth System, Experience More, Specification vol. 0, Covered Core Package Version: 4.0, 2 302 pages (2010).

Tierney, et al., "Effect of Acetaminophen on the Accuracy of Glucose Measurements Obtained with the GlucoWatch Biographer", Diabetes Technology & Therapeutics, 2(2):199-207 (2000).

Townsend, et al., "Getting Started with Bluetooth Low Energy [Book]", O'Reilly, retrieved from https://www.oreilly.com/library/view/getting-started-with/9781491900550/ch01.html on May 5, 2020, 26 pages.

Velho, et al., "Strategies for Calibrating a Subcutaneous Glucose Sensor", Biomed. Biochim. Acta, vol. 48, pp. 957-964 (1989).

Voskerician, et al., "Sensor Biocompatibility and Biofouling in Real-Time Monitoring", Wiley Encyclopedia of Biomedical Engineering, (John Wiley & Sons, Inc.), pp. 1-19 (2006).

Ward, "A Review of the Foreign-body Response to Subcutaneously-implanted Devices: The Role of Macrophages and Cytokines in Biofouling and Fibrosis", Journal of Diabetes Science and Technology, 2(5):768-777 (2008).

Ward, et al., "A new amperometric glucose microsensor: in vitro and short-term in vivo evaluation", Biosensors & Bioelectronics, 17:181-189 (2002).

Yang, et al., "Glucose Biosensors Based on Oxygen Electrode with Sandwich-Type Membranes", Annals of Biomedical Engineering, 23:833-839 (1995).

Yang, et al., "Glucose Biosensors with Enzyme Entrapped in Polymer Coating", Biomedical Instrumentation & Technology, 29(2):125-133 (1995).

Abbott Press Release—"Abbott Receives CE Mark for FreeStyle® Libre, A Revolutionary Glucose Monitoring System for People with Diabetes" retrieved from https://abbott.mediaroom.com/2014-09-03-Abbott-Receives-CE-Mark-for-FreeStyle-Libre-a-Revolutionary-Glucose-Monitoring-System-for-People-with-Diabetes/, Sep. 3, 2014, 3 pages.

Abbott Press Release—"Abbott Receives FDA Approval for the FreeStyle LibrePro™ System, A Revolutionary Diabetes Sensing Technology for Healthcare Professionals to Use with their Patients" retrieved from https://abbott.mediaroom.com/2016-09-28-Abbott-Receives-FDA-Approval-for-the-FreeStyle-Libre-Pro-System-a-Revolutionary-Diabetes-Sensing-Technology-for-Healthcare-Professionals-to-use-with-their-Patients/, Sep. 28, 2016, 5 pages.

Abbott Press Release—"Abbott's FreeStyle® Libre 14 Day Flash Glucose Monitoring System Now Approved in U.S." retrieved from https://abbott.mediaroom.com/2018-07-27-Abbotts-FreeStyle-R-Libre-14-Day-Flash-Glucose-Monitoring-System-Now-Approved-in-U-S/, Jul. 27, 2018, 3 pages.

Abbott v. Dexcom, Jack Griffis Direct Examination, dated Mar. 15, 2024, 38 pages.

Anzhsn, National Horizon Scanning Unit Horizon Scanning Report, "GlucoWatch® G2 Biographer for the non-invasive monitoring of glucose levels", 46 pages, May 2004.

Cather, CGM Frustrations Survey dated Jun. 2020, 37 pages in Abbott Diabetes Care Inc., et al. v. Dexcom, Inc., Case No. 1:21-cv-00977-KAJ (District of Delaware).

Certified Copy U.S. Pat. No. 11,000,216, issued on May 11, 2021, 86 pages.

Clinical Trials, Competitor and Ecosystem Players dated Jun. 25, 2020, 29 pages in Abbott Diabetes Care Inc., et al. v. Dexcom, Inc., Case No. 1:21-cv-00977-KAJ (District of Delaware).

Declaration of Dr. Anthony Edward Cass in Support of Petition for Inter Partes Review of U.S. Pat. No. 11,020,031 in Abbott Diabetes Care Inc. v. Dexcom, Inc., Case No. IPR2024-00890, In the United States Patent and Trademark Office, Before the Patent Trial and Appeal Board, May 10, 2024, 138 pages.

Declaration of Karl R. Leinsing, MSME, PE, in Support of Abbott's Motion for Summary Judgment dated May 19, 2023, 81 pages in Abbott Diabetes Care Inc., et al. v. Dexcom, Inc., Case No. 1:21-cv-00977-KAJ (District of Delaware).

Design Concepts, Project Status Update for Glucose Sensor Applicator, Dexcom, dated Apr. 21, 2014, 6 pages.

Direct Examination of Neil Sheehan, filed May 31, 2024, ADC-1 (30 pages) & ADC-2 (30 pages).

Effectiveness and Safety Study of the DexCom™ G4 Continuous Glucose Monitoring System, DexCom, Inc., U.S. National Library of Medicine, ClinicalTrials.gov Identifier: NCT01111370, 4 pages (2017).

Design U.S. Appl. No. 29/101,218, filed Feb. 25, 1999, 11 pages.

(56)         References Cited

OTHER PUBLICATIONS

Fraser, "An Introduction to in vivo Biosensing: Progress and Problems", Biosensors in the Body: Continuous In Vivo Monitoring, pp. 1-56 (1997).
FreeStyle Libre 2 HCP Pulse, Mar. 2021 Report, dated Apr. 13, 2021, 14 pages in *Abbott Diabetes Care Inc., et al.* v. *Dexcom, Inc.*, Case No. 1:21-cv-00977-KAJ (District of Delaware).
Godek, et al., Chapter 2, "The Macrophage in Wound Healing Surrounding Implanted Devices", In Vivo Glucose Sensing, 36 pages (2010).
Gross, et al., "Performance Evaluation of the MiniMed® Continuous Glucose Monitoring System During Patient Home Use", Diabetes Technology & Therapeutics, vol. 2, No. 1, pp. 49-56 (2000).
Heller, "Integrated Medical Feedback Systems for Drug Delivery", American Institute of Chemical Engineers Journal, vol. 51, No. 4, pp. 1054-1066 (2005).
Henning, Chapter 5, "Commercially Available Continuous Glucose Monitoring Systems", In Vivo Glucose Sensing, 50 pages (2010).
Kovatchev, et al., "Evaluating the Accuracy of Continuous Glucose-Monitoring Sensors", Diabetes Care, vol. 27, No. 8, pp. 1922-1928 (2004).
Lesperance, et al., "Calibration of the Continuous Glucose Monitoring System for Transient Glucose Monitoring", Diabetes Technology & Therapeutics, vol. 9, No. 2, pp. 183-190 (2007).
Schlosser, et al., "Biocompatibility of Active Implantable Devices", Biosensors in the Body: Continuous in vivo Monitoring, 34 pages (1997).
Seagrove Partners, International Diabetes Device, 2022 Blue Book dated 2022, 143 pages in *Abbott Diabetes Care Inc., et al.* v. *Dexcom, Inc.*, Case No. 1:21-cv-00977-KAJ (District of Delaware).
Wilson et al., Chapter 1, "Introduction to the Glucose Sensing Problem," In Vivo Glucose Sensing, 32 pages (2010).
Wisniewski, et al., "Characterization of implantable biosensor membrane biofouling", Fresenius J Anal Chem, 366:611-621 (2000).
Declaration of Gary D. Fletcher, Ph.D., dated Oct. 10, 2023 for IPR2023-01409, U.S. Pat. No. 11,202,591 (U.S. Appl. No. 17/221,154).
Dock, E. et al., "Multivariate data analysis of dynamic amperometric biosensor responses from binary analyte mixtures—applications of sensitivity correction algorithms", Talanta, 65, 2005 pp. 298-305.
File history of U.S. Appl. No. 17/221,154, filed Apr. 2, 2021 (Exhibit 1002—Part 1-8, 1093 pages in total).
Klueh, et al., Inflammation and Glucose Sensors: Use of Dexamethasone to Extend Glucose Sensor Function and Life Span in Vivo, Journal of Diabetes Science and Technology, vol. 1, Issue 4, pp. 496-504 (2007).
Opponent's Written Response in Opposition of EP 3 730 045, Sep. 27, 2023, 43 pages.
Shenoi, Introduction to Digital Signal Processing and Filter Design, Wiley (2006) (Exhibit 1035—Part 1 & 2, 46 pages in total).
Smith, The Scientist and Engineer's Guide to Digital Signal Processing, Second Edition, 46 pages (1999).
CN 202211322287.0 Second Office Action, Jun. 23, 2025.
Wilinska, M. E., et al., "Overnight Closed-Loop Insulin Delivery with Model Predictive Control: Assessment of Hypoglycemia and Hyperglycemia Risk Using Simulation Studies", Journal of Diabetes Science and Technology, 2009, vol. 3, No. 5, pp. 1109-1120.
Yeuh, W. R., et al., "Analysis of Tilt Turn Guided Performance with In-Flight Antenna Mask Error Compensation", Shanghai Sky, 1989, No. 1, pp. 52-61.
Abbott Press Release—Abbott Receives CE Mark for FreeStyle® Libre, A Revolutionary Glucose Monitoring System for People with Diabetes—https://abbott.mediaroom.com/2014-09-03-Abbott-Receives-CE-Mark-for-FreeStyle-Libre-a-Revolutionary-Glucose-Monitoring-System-for-People-with, Abbott, 5 pages (2014).
Continuous Glucose Monitoring Systems, Product Reference Guide, Diabetes Health Magazine, Dec. 2006-Jan. 2007, 3 pages.
Das, et al., "Review—Electrochemistry and Other Emerging Technologies for Continuous Glucose Monitoring Devices", ECS Sensors Plus, 20 pages (2022).

Dexcom G6, Continuous Glucose Monitoring System, User Guide, Dexcom, Inc., 346 pages (2022).
Englert, et al., "Skin and Adhesive Issues With Continuous Glucose Monitors: A Sticky Situation", Journal of Diabetes Science and Technology, 8(4):745-751 (2014).
U.S. Appl. No. 13/071,487, filed Mar. 24, 2011, 132 pages.
U.S. Appl. No. 13/071,497, filed Mar. 24, 2011, 162 pages.
U.S. Appl. No. 14/884,622, filed Oct. 15, 2015, 488 pages.
U.S. Appl. No. 17/008,630, filed Aug. 31, 2020, 484 pages.
U.S. Appl. No. 17/017,590, filed Sep. 10, 2020, 486 pages.
Freckmann, et al., "Performance Evaluation of Three Continuous Glucose Monitoring Systems: Comparison of Six Sensors per Subject in Parallel", Journal of Diabetes Science and Technology, 7(4):842-853 (2013).
Hanson, et al., "Comparison of Point Accuracy Between Two Widely Used Continuous Glucose Monitoring Systems", Journal of Diabetes Science and Technology, pp. 1-10 (2024).
Harris, et al., "Common Causes of Glucose Oxidase Instability in In Vivo Biosensing: A Brief Review", Journal of Diabetes Science and Technology, 7(4):1030-1038 (2013).
IPro™ 2, User Guide, Medtronic MiniMed, Inc., 108 pages (2010).
Nichols, et al., "Biocompatible Materials for Continuous Glucose Monitoring Devices", Chem Rev., 113(4), 44 pages (2013).
Rice, et al., "Continuous Measurement of Glucose, Facts and Challenges", Anesthesiology, 116(1):199-204 (2012).
Rigo, et al., "Cutaneous Reactions to Continuous Glucose Monitoring and Continuous Subcutaneous Insulin Infusion Devices in Type I Diabetes Mellitus", Journal of Diabetes Science and Technology, 15(4):786-791 (2021).
Rocchitta, et al., "Enzyme Biosensors for Biomedical Applications: Strategies for Safeguarding Analytical Performances in Biological Fluids", Sensors, 16(6):780, 22 pages (2016).
Seven® Plus Continuous Glucose Monitoring System, User's Guide, DexCom, Inc., 145 pages (2010).
STS® Seven™ Continuous Glucose Monitoring System, User's Guide, DexCom, Inc., 75 pages (2007).
Xu, et al., "Anti-Biofouling Strategies for Long-Term Continuous Use of Implantable Biosensors", Chemosensors, 8(3):66, 30 pages (2020).
E-mail Communication from Christopher M. Dougherty regarding Bi Monthly Global Commercial Insights Meeting dated Dec. 17, 2019, 69 pages in *Abbott Diabetes Care Inc., et al.* v. *Dexcom, Inc.*, Case No. 1:21-cv-00977-KAJ (District of Delaware).
"Abbott Receives CE Mark for Freestyle® Libre, A Revolutionary Glucose Monitoring System for People with Diabetes," 8 pages (2023).
ATTD Program, 4 pages (2009).
Boise, Interview with Dexcom CEO, Dexcom CEO Kevin Sayer Explains G6, 9 pages (2018).
Cambridge Dictionary of American English, Cambridge University Press, 3 pages (2000)—Recess.
DexCom (DXCM) Q1 2018 Results—Earnings Call Transcript, 4 pages (2018).
Dexcom (DXCM) Company Profile, 2017 /Q4 Earnings call transcript, 12 pages (2017).
DexcomG6, Continuous Glucose Monitoring System, User Guide, 22 pages (2020).
Dexcom G6 Continuous Glucose Monitoring System User Guide, 7 pages (2020).
DexcomG6, Start Here, Set up, Dexcom G6 Continuous Glucose Monitoring (CGM) System (G6), 8 pages (2019).
DexcomG6, Using Your G6, 7 pages (Mar. 2020).
Email communication from Sophie Hood, Jan. 24, 2023, 6 pages.
"FDA authorizes first fully interoperable continuous glucose monitoring system, streamlines review pathway for similar devices," FDA News Release, https://www.fda.gov/news-events/press-announcements/fda-authorizes-first-fully-interopeable-continuous-glucose-monitoring-system-streamlines-reviews, 3 pages, Mar. 27, 2018.
Figures for U.S. Pat. No. 10,973,443 issued Apr. 13, 2021, 2 pages.
FreeStyle Navigator Continuous Glucose Monitoring System, Pre Market Approval Letter from the FDA, Mar. 12, 2008, 7 pages.

(56) References Cited

OTHER PUBLICATIONS

Funderburk et al., Joint Declaration, U.S. Appl. No. 15/963,828, 11 pages (2020).

Hall, Interview with Kevin Sayer, President and CEO of Dexcom About the New Dexcom G6, College Diabetes Network, 6 pages (2021).

Hoss et al., "Feasibility of Factory Calibration for Subcutaneous Glucose Sensors in Subjects with Diabetes," Journal of Diabetes Science and Technology 2014, vol. 8(1) 89-94, Diabetes Technology Society Reprints and permissions: sagepub.com/journalsPermissions.nav (2013).

Hoss et al., "Continuous Glucose Monitoring in Subcutaneous Tissue Using Factory-Calibrated Sensors: A Pilot Study," Diabetes Technology & Therapeutics, vol. 12, No. 8, DOI: 10.1089/dia.2010.0051 (2010).

Hoss et al., "Continuous glucose monitoring in the tissue: Do we really need to calibrate in-vivo?," Diabetes Technology & Therapeutics, vol. 11, No. 2, (2009).

IEEE 100 The Authoritative Dictionary of IEEE Standards Terms, 7$^{th}$ Ed., 3 pages (2020).

Merriam-Webster's Collegiate Dictionary, 10$^{th}$ Ed., 4 pages (1999)—Housing and recess.

Merriam-Webster's Collegiate Dictionary, 10th Ed., 4 pages (1999)—Release and retain.

Non-Final Office Action for U.S. Appl. No. 17/030,030 dated Dec. 17, 2020, 17 pages.

Non-Final Office Action for U.S. Appl. No. 14/884,622 dated Jun. 13, 2018, 7 pages.

Notice of Allowance for U.S. Appl. No. 15/963,828 dated Mar. 3, 2021, 32 pages.

Omnipod image, Exhibit 182, 2 pages, Sep. 22, 2022.

Response to Non-Final Office Action for U.S. Appl. No. 15/963,828, filed Dec. 8, 2020, 17 pages.

Response to Restriction Requirement for U.S. Appl. No. 14/884,622, filed Apr. 5, 2018, 15 pages.

Sayer, CGMS Changing Diabetes Management: Kevin Sayer, DIC Interview Transcript, Featuring Steve Freed, 11 pages (2019).

S&P Global Market Intelligence "DexCom, Inc. NasdaqGS:DXCM, Company Conference Presentation," 17 pages (2021).

S&P Global Market Intelligence "DexCom, Inc. NasdaqGS:DXCM, Company Conference Presentation," 10 pages (2020).

S&P Global Market Intelligence "DexCom, Inc. NasdaqGS:DXCM, Company Conference Presentation," 11 pages (2019).

Sonix, Dexcom CEO—Prime Position in Our Market—Mad Money—CNBC.mp4, 4 pages (2023).

The MiniMed Paradigm® Real-Time Insulin Pump and Continuous Glucose Monitoring System, Insulin Pump User Guide, Paradigm® 522 and 722 Insulin Pumps, 25 pages (2008).

Tegnestedt et al., "Levels and sources of sound in the intensive care unit—an observational study of three room types," Acta Anaesthesiol Scand (2013).

The Chambers Dictionary, Chambers Harrap Publidhers Ltd (1998/1999), 4 pages (2000)—Retract.

The New Oxford American Dictionary, Oxford University Press, 3 pages (2001)—Retract.

The New Penguin English Dictionary, Penguin Books, 4 pages (2000)—Recess.

U.S. Food & Drug Administration, "Deciding When to Submit a 510(k) for a Change to an Existing Device, Guidance for Industry and Food and Drug Administration Staff," 78 pages (2017).

U.S. Food & Drug Administration, "Deciding When to Submit a 510(k) for a Software Change to an Existing Device, Guidance for Industry and Food and Drug Administration Staff," 32 pages (2017).

U.S. Pat. No. 10,827,954 issued Nov. 10, 2020, 7 pages.

U.S. Pat. No. 10,973,443 issued Apr. 13, 2021, 22 pages.

Watkin, "An Introduction to Flash Glucose Monitoring," 16 pages (2013).

Webster's New College Dictionary, 2 pages (2001)—Alcove.

Webster's Third New International Dictionary, 5 pages (1993)—Retract.

510(k) Summary of Safety and Effectiveness, CleoTM 90 Infusion Set, 2004, 618 pages.

ACCU-CHEK Softclix Plus Lancet Device retrieved from https://web.archive.org/web/20061018055737/http://www.accu-check.com/us/rewrite/content/en_US/2.1.7.1:10/article/ACCM_general_article_3303.htm, 2006, pp. 1-2.

Accu-Chek® Compact Plus, Blood Glucose Meter, Owner's Booklet, 2008, 100 pages.

Certified U.S. Appl. No. 10/633,367, filed 2003, 97 pages.

Chen, et al., "A novel fault-tolerant sensor system for sensor drift compensation", Sensors and Actuators, A 147:623-632 (2008).

Cleo® 90 Infusion Set Training Guide, 1 page, 2007.

Compact Plus Blood Glucose Meter retrieved from https://web.archive.org/web/20090316065810/http://www.accu-check.com/us/rewrite/content/en_US/2.1.9:0/article/ACCM_general_article_5136.htm, 2009, pp. 1-3.

U.S. Appl. No. 60/587,787, filed 2004, 69 pages.

Garibotto, J. et al., "An Innovative Application of Shape Memory Alloy Technology Yields a Novel Therapeutic Approach to Diabetes Management", Insulet Corporation, 2009.

Gerritsen, et al., "Performance of subcutaneously implanted glucose sensors for continuous monitoring", The Netherlands Journal of Medicine, 54:167-179 (1999).

Insulet OmniPod Insulin Management System 019 UST400 User Manual, 2011, 190 pages.

Kalivas et al., "Compensation for Drift and Interferences in Multicomponent Analysis", Laboratory for Chemometrics, Department of Chemistry, University of Washington, 38 pages (1982).

Medtronic Guardian® Real-Time Continuous Glucose Monitoring System User Guide, 2006, pp. 1-181.

Sen-serter User Guide, Metronic MiniMed, 2006, 96 pages.

Summary of Safety and Effectiveness Data, Continuous Glucose Monitor, FreeStyle Navigator® Continuous Glucose Monitoring System, 2008, 27 pages.

Thévenot et al., "Electrochemical Biosensors: Recommended Definitions and Classification (Technical Report)", Pure Appl. Chem. 71(12):2333-2348 (1999).

U.S. Appl. No. 12/842,013 Office Action mailed Aug. 26, 2015.

U.S. Appl. No. 12/842,013 Office Action mailed Mar. 23, 2016.

U.S. Appl. No. 12/842,013 Office Action mailed Nov. 6, 2014.

Walt et al., "The chemistry of enzyme and protein immobilization with glutaraldehyde", Trends in Analytical Chemistry, 13(10):425-430 (1994).

Zhang, "Investigations of potentially implantable glucose sensors", University of Kansas, 24 pages (1991).

Zisser, "The OmniPod Insulin Management System: the Latest Innovation in Insulin Pump Therapy", Diabetes Ther, 2010, vol. 1, No. 1, pp. 10-24.

Abbott 2023 Annual Report, 86 pages (2023).

Abbott Press Release—"Abbott's FreeStyle Libre® is Named Best Medical Technology in Last 50 Years by the Galien Foundation", 2 pages (2022).

Abbott Press Release—"Abbott's FreeStyle® Libre 2 ICGM Cleared in U.S. for Adults and Children with Diabetes, Achieving Highest Level of Accuracy and Performance Standards", 3 pages (2020).

Abbott Press Release—"FreeStyle Libre Honored by Prix Galien", 4 pages (2019).

Abbott Press Release—"Real-World Data Show Abbott's FreeStyle Libre® Systems and GLP-1 Medicines Work Better Together for People with Type 2 Diabetes", 2 pages (2024).

Ahn, "Abbott's Euro Approved Wearable Glucose Monitor is Different than Anything on the Market", 6 pages (2014).

CES 2022 Innovation Award Product, Innovation Awards Honorees, FreeStyle Libre 3 System, 1 page (2022).

Chicago Innovation Awards—Abbott Laboratories, retrieved from: https://chicagoinnovation.com/winners/abbott-laboratories/, 5 pages (2018).

Deposition of Gary Fletcher, Ph.D., dated Jun. 26, 2024, 54 pages in *Abbott Diabetes Care Inc., et al.* v. *Dexcom, Inc.*, Case No. 03946-82752US01, In the United States District Court for the District of Delaware.

Dexcom G5 Mobile, Continuous Glucose Monitoring System, Quick Start Guide, Dexcom, 36 pages (2020).

(56) References Cited

OTHER PUBLICATIONS

Dexcom G6, Start Here, Set up Guide, Dexcom, 20 pages (2022).
Dexcom G7, Overview Webpage, retrieved from: https://www.dexcom.com/g7-cgm-system, 20 pages (2024).
Dexcom G7, User Guide, Dexcom, 196 pages (2024).
Diabetes Product Review: Abbott FreeStyle Libre Flash Glucose Monitor, DiabetesMine, 6 pages (2017).
Ex Parte Reexamination Certificate for U.S. Pat. No. 10,959,654, certificate issued on Aug. 5, 2024, 2 pages.
FreeStyle Libre 14 day, "Your FreeStyle Libre 14 day System", In-Service Guide, Abbott, 28 pages (2021).
FreeStyle Libre 2, Get Started, Your guide to the FreeStyle Libre 2 system, Abbott, 15 pages (2023).
FreeStyle Libre 3 Continuous Glucose Monitoring System, User's Manual, Abbott, 248 pages (Part 1—124 pages and Part 2—124 pages) (2023).
FreeStyle Libre 3 Flash Glucose Monitoring System, Get Started with the FreeStyle Libre 3 System, Abbott, 11 pages (2023).
FreeStyle Libre FAQs, retrieved from https://www.freestyle.abbott/uk-en/support/faq/question-answer.html?q=UKFaqquestion-55#, 2 pages (2024).
Galien Golden Jubilee Webpage—https://www.galienfoundation.org/galien-golden-jubilee, 3 pages (2022).
German Innovation Award—FreeStyle Libre 2—Measure Sugar without Piercing Using a Sensor and App, 1 page (2020).
Gomez et al., "Overview and Evaluation of Bluetooth Low Energy: An Emerging Low-Power Wireless Technology" Sensors, 2012, pp. 11734-11753.
Gonzales, et al., "The Progress of Glucose Monitoring—A Review of Invasive to Minimally and Non-Invasive Techniques, Devices and Sensors", Sensors, 19(4):800, 45 pages (2019).
Good Design Award—2017 Good Design Award, Abbott Japan Co., Ltd., Glucose Monitoring Systems, FreeStyle Libre, 9 pages (2017).
Gough, et al., "Perspectives in Diabetes, Development of the Implantable Glucose Sensor, What Are the Prospects and Why Is It Taking So Long?", Diabetes, vol. 44, pp. 1005-1009 (1995).
Hermanides, et al., "Current Application of Continuous Glucose Monitoring in the Treatment of Diabetes", Diabetes Care, vol. 34, Supp. 2, pp. S197-S201 (2011).
Joseph, et al., "Glucose Sensing in the Subcutaneous Tissue: Attempting to Correlate the Immune Response with Continuous Glucose Monitoring Accuracy", Diabetes Technology & Therapeutics, vol. 20, No. 5, pp. 321-324 (2018).
Letter from the U.S. Food & Drug Administration to Dexcom, Inc. regarding the Dexcom G7 Continuous Glucose Monitoring (CGM) System, 510(k) Premarket Notification and 510(k) summary, 10 pages, Dec. 7, 2022.
Lovett, "What's Next for Dexcom? CEO, CTO Talk G6 for Inpatient Use, Expanding CGMs for Patients without Diabetes", Global Edition, Digital Health, 17 pages (2020).
Medical Design Excellence Awards®, "27 Winners Announced at the 19th Annual Medical Design Excellence Awards (MDEA) Award Ceremony", 4 pages (2017).
News Release—Abbott—"BinaxNOW, FreeStyle Libre 2 Win Big Innovation Honors", 6 pages (2021).
News Release—Abbott Ireland—"Abbott's FreeStyle Libre Flash Glucose Monitoring System Wins the IMSTA Most Innovative Product Multi-National Award 2017", 2 pages (2017).
News Release—Business Intelligence Group—"55 Chosen as Winners in Annual Big Innovation Awards", 3 pages (2018).
News Release—Edison Awards—"Edison Awards Announces 2016 Gold, Silver, and Bronze Awards Winners", 9 pages (2016).
Not Just a Patch, Dexcom G7 Release: The Most Exciting New Features, "Dexcom G7: These are the Most Exciting Features", 14 pages (2024).
Padgette et al., "Guide to Bluetooth Security, Recommendations of the National Institute of Standards and Technology," NET Special Publication 800421 Revision National Institute of Standards and Technology, U.S. Department of Commerce, 48 pages (2012).

Press Release—"Abbott's FreeStyle Libre® 3 Receives U.S. FDA Clearance—Features World's Smallest, Thinnest and Most Accurate 14-Day Glucose Sensor", 3 pages (2022).
The Edison Awards—About US, Recognizing Global Innovation Excellence, 3 pages (2024).
The Edison Awards—Edison Best New Product Awards, 2022 Winners, 52 pages (2022).
The Edison Awards—Edison Best New Product Awards™, 2021 Winners, 19 pages (2024).
Van den Boom, et al., "Changes in the utilization of blood glucose test strips among patients using intermittent—scanning continuous glucose monitoring in Germany", Diabetes Obes Metab., 22:922-928 (2020).
Abbott Diabetes Patents, FreeStyle Libre® Glucose Monitoring System, FreeStyle Libre® 2 Glucose Monitoring System and FreeStyle Libre® 3 Glucose Monitoring System, Abbott, 2024, 6 pages.
Burge et al., "Continuous Glucose Monitoring: The Future of Diabetes Management", Diabetes Spectrum, vol. 21, No. 2, 2008, pp. 112-119.
Clancy, et al., A new device for assessing changes in skin viscoelasticity using indentation and optical Measurement Skin Research and Technology, 2010, 16:210-228.
Cleo™ 90 Infusion Set Training Guide, 2006 1 page.
Dexcom, Instructions for Use, DexCom™ STS™ Sensor, 2006, 51 pages.
DexCom™ STS™ Continuous Glucose Monitoring System, User's Guide, 2006, 58 pages.
FDA, U.S. Food & Drug Administration, Premarket Approval (PMA), Dexcom STS Continuous Monitor, 2006 1 page.
File History of U.S. Pat. No. 7,731,691, issued Jun. 8, 2010, 739 pages.
File History of U.S. Trademark Registration No. 3,154,910, Registered Oct. 10, 2006, 67 pages.
FreeStyle Navigator Continuous Glucose Monitoring System, Abbott 2008, 191 pages.
Letter from the Department of Health & Human Services, Food and Drug Administration to Mr. David H. Short at Smiths Medical MD, Incorporated re the Cleo 90 Infusion Set, Section 510(k) No. K042172, Premarket Notification dated Oct. 7, 2004, 3 pages.
Mazze et al., "Evaluating the Accuracy, Reliability, and Clinical Applicability of Continuous Glucose Monitoring (CGM): Is CGM Ready for Real Time?" Diabetes Technology & Therapeutics, 2009, vol. 11, No. 1, pp. 11-18.
Medtronic, Introducing the Guardian® Real-Time Continuous Glucose Monitoring System, 2007, 3 pages.
Piper et al., Real Time Continuous Glucose Monitoring in Pediatric Patients During and After Cardiac Surgery, Pediatrics, Official Journal of the American Academy of Pediatrics, 2006, pp. 1176-1184.
Rabiee et al., "Numerical and Clinical Accuracy of a Continuous Glucose Monitoring System during Intravenous Insulin Therapy in the Surgical and Burn Intensive Care Units", Journal of Diabetes Science and Technology, 2009, pp. 951-959.
Sacks, et al., "Skin blood flow changes and tissue deformations produced by cylindrical indentors" Journal of Rehabilitation Research and Developments, 1985, 6 pages.
Schneider et al., "Evaluating the use of the Cleo® 90 infusion set for patients on a palliative care unit", International Journal of Palliative Nursing, 2009, pp. 372-376.
Table of Contents, Skin research & Technology, 2010, 8 pages.
The Wayback Machine, Cleo 90 infusion set, 2006, 1 page.
The Wayback Machine, DexCom Products, The Seven System, DexCom, 2007, 2 pages.
The Wayback Machine, Dexcom, User Manuals, 2007, 2 pages.
The Wayback Machine, FDA, US Food and Drug Administration, PMA FreeStyle Navigator Continuous Glucose Monitor PMA No. P050020, 2008 2 pages.
The Wayback Machine, FreeStyle Navigator Continuous Glucose Monitoring System, Answers to Frequently Asked Questions, Abbott Laboratories, 2008, 1 page.
The Wayback Machine, FreeStyle Navigator® Continuous Glucose Monitoring System, Answers to Frequently Asked Questions, Abbott Laboratories, 2007, 2 pages.

(56) References Cited

OTHER PUBLICATIONS

The Wayback Machine, Guardian® Real-Time System, Features, Medtronic MiniMed, Inc., 2007, 4 pages.

The Wayback Machine, Introducing the new FreeStyle Navigator® Continuous Glucose Monitoring System, 2007, 2 pages.

The Wayback Machine, Medtronic Diabetes, Main Webpage, 2007, 1 page.

The Wayback Machine, Medtronic, Product Information, We are the Leader in Diabetes Management, Medtronic MiniMed, Inc., 2007, 2 pages.

The Wayback Machine, Smiths Medical Cleo 90 Infusion Set, Ambulatory Infusion Disposables, 2022, 2 pages.

The Wayback Machine, smiths-medical is now part of ICU Medical, 2022, 2 pages.

The Wayback Machine, smiths-medical, New & Events, 2006, 1 page.

The Wayback Machine, smiths-medical, Products and Promotions, 2006, 1 page.

The Wayback Machine, smiths-medical, Smiths Medical Latest News, 2006, 2 pages.

U.S. Dept. Health & Human Services, FDA, 510(k) Premarket Notification, CLEO 90 Infusion Set, 2004 1 page.

U.S. Dept. of Veterans Affairs, Journal of Rehabilitation Research & Development, 1980, 3 pages.

Dorland's Illustrated Medical 31$^{st}$ Edition Dictionary, definition of "fluid, intersitial", (2007), 3 pages.

Forlenza, G.P., et al., "Factory-Calibrated Continuous Glucose Monitoring: How and Why It Works, and the Dangers of Reuse Beyond Approved Duration of Wear", Diabetes Technology & Therapeutics, vol. 21, No. 4, (2019) 13 pages.

Koschinsky T., et al., "Sensors for glucose monitoring: technical and clinical aspects" Diabetes/Metabolism Research and Reviews, 17 (2001) 113-123.

Lodwig, V., et al., "Continuous Glucose Monitoring with Glucose Sensors: Calibration and Assessment Criteria", Diabetes Technology & Therapeutics, vol. 5, No. 4, (2003) pp. 573-587.

Stephens Inc., Research Bulletin, "DexCom, Inc., A True Game Changer: The G6 Eliminates Fingersticks", (2018) 5 pages.

The American Hertiage® Medical Dictionary, definition of "catheter" and "interstitial fluid", (2007), 4 pages.

DexcomG7, Start Here, Operational Manual, Dexcom, Inc. 9 pages (2022) (with an English abstract).

DexcomG7, Receiver: Start Here, Operational Manual, Dexcom, Inc., 8 pages (2022).

DexcomG7, Operational Manual, User Guide, Dexcom, Inc., 179 pages (2022) (with an English abstract).

Dexcom, Inserting Sensor, Instructions for Use, Dexcom, Inc., 2 pages (2021).

U.S. Appl. No. 60/587,787, filed Jul. 13, 2004, 69 pages.

U.S. Appl. No. 60/687,199, filed Jun. 2, 2005, Ward, et al.

U.S. Appl. No. 61/155,889, filed Feb. 26, 2009, Hoss, et al.

Abel et al., "Biosensors for in vivo glucose measurement: can we cross the experimental stage", Biosensors and Bioelectronics, 17:1059-1070 (2002).

Atanasov et al., "Implantation of a refillable glucose monitoring-telemetry device", Biosensors & Bioelectronics, 12(7):669-680 (1997).

Bindra, "Development of potentially implantable glucose sensors", The University of Arizona, 227 pages (1990).

Choleau et al., "Calibration of a subcutaneous amperometric glucose sensor implanted for 7 days in diabetic patients Part 2. Superiority of the one-point calibration method", Biosensors and Bioelectronics, 17:647-654 (2002).

FreeStyle Navigator Continuous Glucose Monitoring System, User's Guide, Abbott Diabetes Care Inc., 38 pages (2008).

Frost, et al., "Implantable chemical sensors for real-time clinical monitoring: progress and challenges", Current Opinion in Chemical Biology, 6:633-641 (2002).

Guardian® Real-Time, Continuous Glucose Monitoring System, User Guide, Medtronic MiniMed, Inc., 184 pages (2006).

Kerner et al., The function of a hydrogen peroxide-detecting electroenzymatic glucose electrode is markedly impaired in human sub-cutaneous tissue and plasma, Biosensors & Bioelectronics, 8:473-482 (1993).

Koschinsky et al., "Sensors for glucose monitoring: technical and clinical aspects", Diabetes/Metabolism Research and Reviews, 17:113-123 (2001).

Koschwanez et al., "In vitro, in vivo and post explantation testing of glucose-detecting biosensors: Current methods and recommendations", Biomaterials, 28:3687-3703 (2007).

OmniPod Insulin Management System, UST400, User Guide, Insulet Corporation, 190 pages (2011).

Moussy et al. "Performance of Subcutaneously Implanted Needle-Type Glucose Sensors Employing a Novel Trilayer Coating", Anal. Chem., 65:2072-2077 (1993).

Pickup et al., "In vivo glucose sensing for diabetes management: progress towards non-invasive monitoring", BMJ, 319, pp. 1-4 (1999).

Pickup et al., "Responses and calibration of amperometric glucose sensors implanted in the subcutaneous tissue of man", Acta Diabetol, 30:143-148 (1993).

Ward et al., "Rise in background current over time in a subcutaneous glucose sensor in the rabbit: relevance to calibration and accuracy", Biosensors & Bioelectronics, 15:53-61 (2000).

Wilson et al., "Biosensors for real-time in vivo measurements", Biosensors and Bioelectronics, 20:2388-2403 (2005).

Wisniewski et al., "Analyte flux through chronically implanted subcutaneous polyamide membranes differs in humans and rats", Am J Physiol Endocrinol Metab, 282:E1316-E1323 (2002).

* cited by examiner

SYSTEMS, DEVICES, AND METHODS WITH DURATION-BASED ADJUSTMENT OF SENSOR DATA

CROSS-REFERENCE TO RELATED APPLICATIONS

The present application is a continuation of U.S. patent application Ser. No. 16/204,358 filed Nov. 29, 2018, which is a continuation of International Patent Application No. PCT/US2018/030619, filed May 2, 2018, which claims priority to and the benefit of U.S. Provisional Patent Application No. 62/500,955, filed May 3, 2017, and U.S. Provisional Patent Application No. 62/624,665, filed Jan. 31, 2018, all of which are incorporated by reference herein in their entirety for all purposes.

FIELD

The subject matter described herein relates generally to systems, devices, and methods for performing duration-based adjustments of sensor data, and more particularly, to the improvement of analyte monitoring systems with analyte sensors that are subjected to various durations of post-manufacture storage and various durations of active (e.g., in vivo) use.

BACKGROUND

A vast and growing market exists for monitoring the health and condition of humans and other living animals. Information that describes the physical or physiological condition of humans can be used in countless ways to assist and improve quality of life and diagnose and treat undesirable human conditions.

A common device used to collect such information is a physiological sensor such as a biochemical analyte sensor, or a device capable of sensing a chemical analyte of a biological entity. Biochemical sensors come in many forms and can be used to sense analytes in fluids, tissues, or gases forming part of or produced by a biological entity, such as a human being. These analyte sensors can be used on or within the body itself, or they can be used on biological substances that have already been removed from the body.

The performance of an analyte sensor can be characterized in a number of ways, and a characteristic of particular importance can be the accuracy of the analyte sensor, or the degree to which the sensor correctly measures the concentration or content of the chemical analyte being measured.

Although analyte sensors often have a complex and well-studied design, they can still be subject to a degree of performance variation. For these and other reasons, needs exist for improvement to the performance of analyte sensors.

SUMMARY

Example embodiments of systems, devices, and methods are described herein for improving the performance of analyte sensors. These embodiments provide for the adjustment or calibration of data collected with analyte sensors based on one or more durations of time. A first example duration of time for which these embodiments can compensate pertains to changes in sensor response due to the period of time post-manufacture before a particular analyte sensor is put into use, e.g., a shelf duration. A second example duration of time for which these embodiments can compensate pertains to changes in sensor response due to the period of time during which the analyte sensor is used, e.g., a wear duration. Numerous examples of algorithms and methods for performing variations of one or both of these compensations are provided, as well as example embodiments of systems and devices for performing the same. Numerous example embodiments of various methods for measuring the time durations, and systems and devices for performing the same, are provided. Example embodiments compensating for other variables that can change sensor response, such as temperature, in addition to one or both durations of time are also provided, in addition to systems and devices for performing the same.

Other systems, devices, methods, features and advantages of the subject matter described herein will be or will become apparent to one with skill in the art upon examination of the following figures and detailed description. It is intended that all such additional systems, methods, features and advantages be included within this description, be within the scope of the subject matter described herein, and be protected by the accompanying claims. In no way should the features of the example embodiments be construed as limiting the appended claims, absent express recitation of those features in the claims.

BRIEF DESCRIPTION OF FIGURES

The details of the subject matter set forth herein, both as to its structure and operation, may be apparent by study of the accompanying figures, in which like reference numerals refer to like parts. The components in the figures are not necessarily to scale, emphasis instead being placed upon illustrating the principles of the subject matter. Moreover, all illustrations are intended to convey concepts, where relative sizes, shapes and other detailed attributes may be illustrated schematically rather than literally or precisely.

DETAILED DESCRIPTION

Figure 1A:
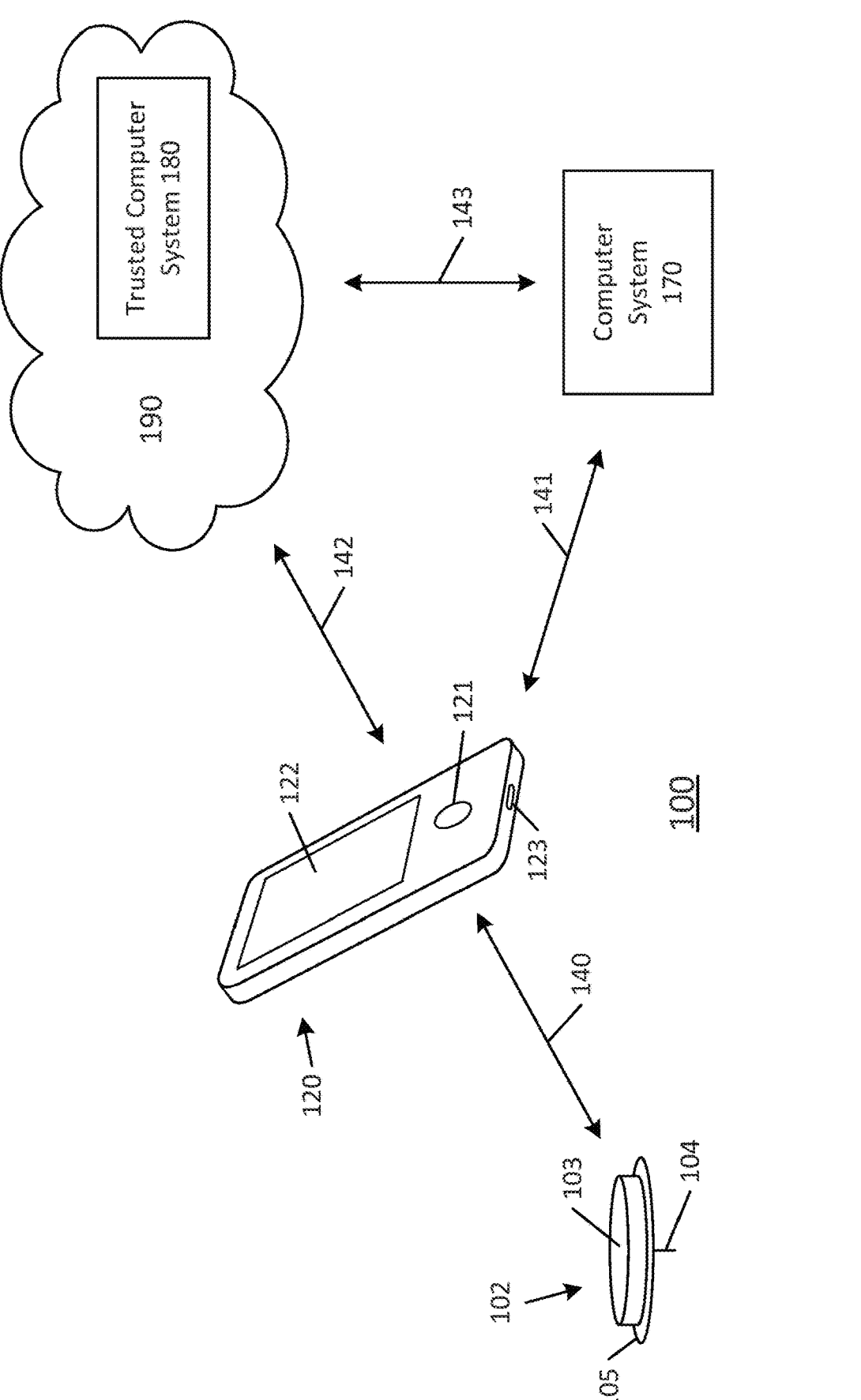
FIG. 1A is an illustrative view depicting an example embodiment of an in vivo analyte monitoring system.

Before the present subject matter is described in detail, it is to be understood that this disclosure is not limited to the particular embodiments described, as such may, of course, vary. It is also to be understood that the terminology used herein is for the purpose of describing particular embodiments only, and is not intended to be limiting, since the scope of the present disclosure will be limited only by the appended claims.

Generally, embodiments of the present disclosure are used with systems, devices, and methods for detecting at least one analyte, such as glucose, in a bodily fluid (e.g., subcutaneously within the interstitial fluid ("ISF") or blood, within the dermal fluid of the dermal layer, or otherwise). Accordingly, many embodiments include in vivo analyte sensors structurally configured so that at least a portion of the sensor is, or can be, positioned in the body of a user to obtain information about at least one analyte of the body. However, the embodiments disclosed herein can be used with in vivo analyte monitoring systems that incorporate in vitro capability, as well as purely in vitro or ex vivo analyte monitoring systems, including those systems that are entirely non-invasive.

Before describing the embodiments in detail, however, it is first desirable to describe examples of devices that can be present within, for example, an in vivo analyte monitoring system, as well as examples of their operation, all of which can be used with the embodiments described herein.

Example Embodiments of Analyte Monitoring Systems

There are various types of analyte monitoring systems. "Continuous Analyte Monitoring" systems (or "Continuous Glucose Monitoring" systems), for example, are in vivo systems that can transmit data from a sensor control device to a reader device repeatedly or continuously without prompting, e.g., automatically according to a schedule. "Flash Analyte Monitoring" systems (or "Flash Glucose Monitoring" systems or simply "Flash" systems), as another example, are in vivo systems that can transfer data from a sensor control device in response to a scan or request for data by a reader device, such as with a Near Field Communication (NFC) or Radio Frequency Identification (RFID) protocol. In vivo analyte monitoring systems can also operate without the need for finger stick calibration.

In vivo monitoring systems can include a sensor that, while positioned in vivo, makes contact with the bodily fluid of the user and senses one or more analyte levels contained therein. The sensor can be part of a sensor control device that resides on the body of the user and contains the electronics and power supply that enable and control the analyte sensing. The sensor control device, and variations thereof, can also be referred to as a "sensor control unit," an "on-body electronics" device or unit, an "on-body" device or unit, or a "sensor data communication" device or unit, to name a few. As used herein, these terms are not limited to devices with analyte sensors, and encompass devices that have sensors of other types, whether biometric or non-biometric. The term "on body" refers to any device that resides directly on the body or in close proximity to the body, such as a wearable device (e.g., glasses, watch, wristband or bracelet, neckband or necklace, etc.).

In vivo monitoring systems can also include one or more reader devices that receive sensed analyte data from the sensor control device. These reader devices can process and/or display the sensed analyte data, in any number of forms, to the user. These devices, and variations thereof, can be referred to as "handheld reader devices," "reader devices" (or simply, "readers"), "handheld electronics" (or handhelds), "portable data processing" devices or units, "data receivers," "receiver" devices or units (or simply receivers), "relay" devices or units, or "remote" devices or units, to name a few. Other devices such as personal computers have also been utilized with or incorporated into in vivo and in vitro monitoring systems.

In vivo analyte monitoring systems can be differentiated from "in vitro" systems that contact a biological sample outside of the body (or rather "ex vivo") and that typically include a meter device that has a port for receiving an analyte test strip carrying a bodily fluid of the user, which can be analyzed to determine the user's analyte level. As mentioned, the embodiments described herein can be used with in vivo systems, in vitro systems, and combinations thereof.

The embodiments described herein can be used to monitor and/or process information regarding any number of one or more different analytes. Analytes that may be monitored include, but are not limited to, acetyl choline, amylase, bilirubin, cholesterol, chorionic gonadotropin, glycosylated hemoglobin (HbAlc), creatine kinase (e.g., CK-MB), creatine, creatinine, DNA, fructosamine, glucose, glucose derivatives, glutamine, growth hormones, hormones, ketones, ketone bodies, lactate, peroxide, prostate-specific antigen, prothrombin, RNA, thyroid stimulating hormone, and troponin. The concentration of drugs, such as, for example, antibiotics (e.g., gentamicin, vancomycin, and the like), digitoxin, digoxin, drugs of abuse, theophylline, and warfarin, may also be monitored. In embodiments that monitor more than one analyte, the analytes may be monitored at the same or different times FIG. 1A is an illustrative view depicting an example embodiment of an in vivo analyte monitoring system 100 having a sensor control device 102 and a reader device 120 that communicate with each other over a local communication path (or link) 140, which can be wired or wireless, and uni-directional or bi-directional. In embodiments where path 140 is wireless, a near field communication (NFC) protocol, RFID protocol, Bluetooth or Bluetooth Low Energy protocol, Wi-Fi protocol, proprietary protocol, or the like can be used, including those communication protocols in existence as of the date of this filing or their later developed variants.

Reader device 120 is also capable of wired, wireless, or combined communication with a computer system 170 (e.g., a local or remote computer system) over communication path (or link) 141 and with a network 190, such as the internet or the cloud, over communication path (or link) 142. Communication with network 190 can involve communication with trusted computer system 180 within network 190, or though network 190 to computer system 170 via communication link (or path) 143. Communication paths 141, 142, and 143 can be wireless, wired, or both, can be uni-directional or bi-directional, and can be part of a telecommunications network, such as a Wi-Fi network, a local area network (LAN), a wide area network (WAN), the internet, or other data network. In some cases, communication paths 141 and 142 can be the same path. All communications over paths 140, 141, and 142 can be encrypted and sensor control device 102, reader device 120, computer system 170, and trusted computer system 180 can each be configured to encrypt and decrypt those communications sent and received.

Variants of devices 102 and 120, as well as other components of an in vivo-based analyte monitoring system that are suitable for use with the system, device, and method embodiments set forth herein, are described in U.S. Patent Application Publ. No. 2011/0213225 (the '225 Publication), which is incorporated by reference herein in its entirety for all purposes.

Sensor control device 102 can include a housing 103 containing in vivo analyte monitoring circuitry and a power source. In this embodiment, the in vivo analyte monitoring circuitry is electrically coupled with an analyte sensor 104 that extends through an adhesive patch 105 and projects away from housing 103. Adhesive patch 105 contains an adhesive layer (not shown) for attachment to a skin surface of the body of the user. Other forms of body attachment to the body may be used, in addition to or instead of adhesive.

Sensor 104 is adapted to be at least partially inserted into the body of the user, where it can make fluid contact with that user's bodily fluid (e.g., subcutaneous (subdermal) fluid, dermal fluid, or blood) and be used, along with the in vivo analyte monitoring circuitry, to measure analyte-related data of the user. Sensor 104 and any accompanying sensor control electronics can be applied to the body in any desired manner. For example, an insertion device (not shown) can be used to position all or a portion of analyte sensor 104 through an external surface of the user's skin and into contact with the user's bodily fluid. In doing so, the insertion device can also position sensor control device 102 with adhesive patch 105 onto the skin. In other embodiments, insertion device can position sensor 104 first, and then accompanying sensor control electronics can be coupled with sensor 104 afterwards, either manually or with the aid of a mechanical device. Examples of insertion devices are described in U.S. Publication Nos. 2008/0009692, 2011/0319729, 2015/0018639, 2015/0025345, and 2015/0173661, all which are incorporated by reference herein in their entireties and for all purposes.

After collecting raw data from the user's body, sensor control device 102 can apply analog signal conditioning to the data and convert the data into a digital form of the conditioned raw data. In some embodiments, this conditioned raw digital data can be encoded for transmission to another device, e.g., reader device 120, which then algorithmically processes that digital raw data into a final form representative of the user's measured biometric (e.g., a form readily made suitable for display to the user). This algorithmically processed data can then be formatted or graphically processed for digital display to the user. In other embodiments, sensor control device 102 can algorithmically process the digital raw data into the final form that is representative of the user's measured biometric (e.g., analyte level) and then encode and wirelessly communicate that data to reader device 120, which in turn can format or graphically process the received data for digital display to the user. In other embodiments, sensor control device 102 can graphically process the final form of the data such that it is ready for display, and display that data on a display of sensor control device 102 or transmit the data to reader device 120. In some embodiments, the final form of the biometric data (prior to graphic processing) is used by the system (e.g., incorporated into a diabetes monitoring regime) without processing for display to the user. In some embodiments, sensor control device 102 and reader device 120 transmit the digital raw data to another computer system for algorithmic processing and display.

Reader device 120 can include a display 122 to output information to the user and/or to accept an input from the user, and an optional input component 121 (or more), such as a button, actuator, touch sensitive switch, capacitive switch, pressure sensitive switch, jog wheel or the like, to input data, commands, or otherwise control the operation of reader device 120. In certain embodiments, display 122 and input component 121 may be integrated into a single component, for example, where the display can detect the presence and location of a physical contact touch upon the display, such as a touch screen user interface. In certain embodiments, input component 121 of reader device 120 may include a microphone and reader device 120 may include software configured to analyze audio input received from the microphone, such that functions and operation of the reader device 120 may be controlled by voice commands. In certain embodiments, an output component of reader device 120 includes a speaker (not shown) for outputting information as audible signals. Similar voice responsive components such as a speaker, microphone and software routines to generate, process and store voice driven signals may be included in sensor control device 102.

Reader device 120 can also include one or more data communication ports 123 for wired data communication with external devices such as computer system 170 or sensor control device 102. Example data communication ports include USB ports, mini USB ports, USB Type-C ports, USB micro-A and/or micro-B ports, RS-232 ports, Ethernet ports, Firewire ports, or other similar data communication ports configured to connect to the compatible data cables. Reader device 120 may also include an integrated or attachable in vitro glucose meter, including an in vitro test strip port (not shown) to receive an in vitro glucose test strip for performing in vitro blood glucose measurements.

Reader device 120 can display the measured biometric data wirelessly received from sensor control device 102 and can also be configured to output alarms, alert notifications, glucose values, etc., which may be visual, audible, tactile, or any combination thereof. Further details and other display embodiments can be found in, e.g., U.S. Publication No. 2011/0193704, which is incorporated herein by reference in its entirety for all purposes.

Reader device 120 can function as a data conduit to transfer the measured data from sensor control device 102 to computer system 170 or trusted computer system 180. In certain embodiments, the data received from sensor control device 102 may be stored (permanently or temporarily) in one or more memories of reader device 120 prior to uploading to system 170, 180 or network 190.

Computer system 170 may be a personal computer, a server terminal, a laptop computer, a tablet, or other suitable data processing device. Computer system 170 can be (or include) software for data management and analysis and communication with the components in analyte monitoring system 100. Computer system 170 can be used by the user or a medical professional to display and/or analyze the biometric data measured by sensor control device 102. In some embodiments, sensor control device 102 can communicate the biometric data directly to computer system 170 without an intermediary such as reader device 120, or indirectly using an internet connection (also optionally without first sending to reader device 120). Operation and use of computer system 170 is further described in the '225 Publication incorporated herein. Analyte monitoring system 100 can also be configured to operate with a data processing module (not shown), also as described in the incorporated '225 Publication.

Trusted computer system 180 can be within the possession of the manufacturer or distributor of sensor control device 102, either physically or virtually through a secured connection, and can be used to perform authentication of sensor control device 102, for secure storage of the user's biometric data, and/or as a server that serves a data analytics program (e.g., accessible via a web browser) for performing analysis on the user's measured data.

Example Embodiments of Reader Devices

Reader device 120 can be a mobile communication device such as a dedicated reader device (configured for communication with a sensor control device 102, and optionally a computer system 170, but without mobile telephony communication capability) or a mobile telephone including, but not limited to, a Wi-Fi or internet enabled smart phone, tablet, or personal digital assistant (PDA). Examples of smart phones can include those mobile phones based on a Windows® operating system, Android™ operating system, iPhone® operating system, Palm® WebOS™, Blackberry® operating system, or Symbian® operating system, with data network connectivity functionality for data communication over an internet connection and/or a local area network (LAN).

Reader device 120 can also be configured as a mobile smart wearable electronics assembly, such as an optical assembly that is worn over or adjacent to the user's eye (e.g., a smart glass or smart glasses, such as Google glasses, which is a mobile communication device). This optical assembly can have a transparent display that displays information about the user's analyte level (as described herein) to the user while at the same time allowing the user to see through the display such that the user's overall vision is minimally obstructed. The optical assembly may be capable of wireless communications similar to a smart phone. Other examples of wearable electronics include devices that are worn around or in the proximity of the user's wrist (e.g., a watch, etc.), neck (e.g., a necklace, etc.), head (e.g., a headband, hat, etc.), chest, or the like.

Figure 1B:
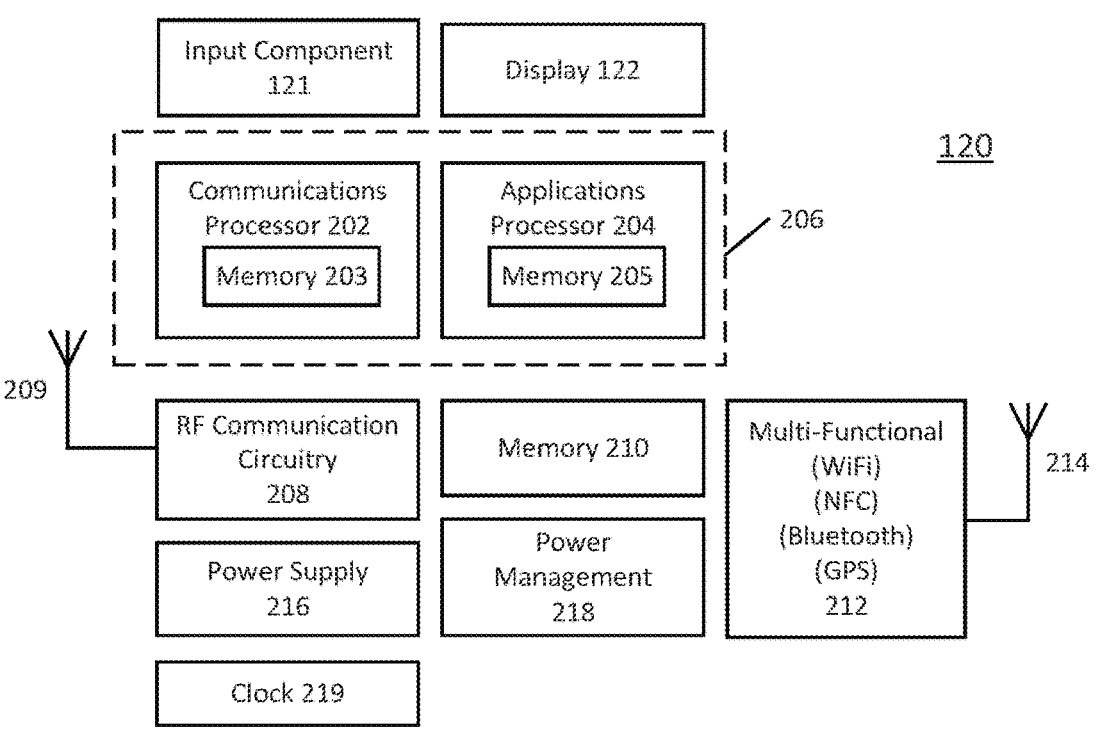
FIG. 1B is a block diagram of an example embodiment of a reader device.

FIG. 1B is a block diagram of an example embodiment of a reader device 120 configured as a smart phone. Here, reader device 120 includes an input component 121, display 122, and processing circuitry 206, which can include one or more processors, microprocessors, controllers, and/or microcontrollers, each of which can be a discrete chip or distributed amongst (and a portion of) a number of different chips. Here, processing circuitry 206 includes a communications processor 202 having on-board memory 203 and an applications processor 204 having on-board memory 205. Reader device 120 further includes RF communication circuitry 208 coupled with an RF antenna 209, a memory 210, multi-functional circuitry 212 with one or more associated antennas 214, a power supply 216, power management circuitry 218, and a clock 219. FIG. 1B is an abbreviated representation of the typical hardware and functionality that resides within a smart phone and those of ordinary skill in the art will readily recognize that other hardware and functionality (e.g., codecs, drivers, glue logic) can also be included.

Communications processor 202 can interface with RF communication circuitry 208 and perform analog-to-digital conversions, encoding and decoding, digital signal processing and other functions that facilitate the conversion of voice, video, and data signals into a format (e.g., in-phase and quadrature) suitable for provision to RF communication circuitry 208, which can then transmit the signals wirelessly. Communications processor 202 can also interface with RF communication circuitry 208 to perform the reverse functions necessary to receive a wireless transmission and convert it into digital data, voice, and video. RF communication circuitry 208 can include a transmitter and a receiver (e.g., integrated as a transceiver) and associated encoder logic.

Applications processor 204 can be adapted to execute the operating system and any software applications that reside on reader device 120, process video and graphics, and perform those other functions not related to the processing of communications transmitted and received over RF antenna 209. The smart phone operating system will operate in conjunction with a number of applications on reader device 120. Any number of applications (also known as "user interface applications") can be running on reader device 120 at any one time, and may include one or more applications that are related to a diabetes monitoring regime, in addition to the other commonly used applications that are unrelated to such a regime, e.g., email, calendar, weather, sports, games, etc. For example, the data indicative of a sensed analyte level and in vitro blood analyte measurements received by the reader device can be securely communicated to user interface applications residing in memory 210 of reader device 120. Such communications can be securely performed, for example, through the use of mobile application containerization or wrapping technologies.

Memory 210 can be shared by one or more of the various functional units present within reader device 120, or can be distributed amongst two or more of them (e.g., as separate memories present within different chips). Memory 210 can also be a separate chip of its own. Memories 203, 205, and 210 are non-transitory, and can be volatile (e.g., RAM, etc.) and/or non-volatile memory (e.g., ROM, flash memory, F-RAM, etc.).

Multi-functional circuitry 212 can be implemented as one or more chips and/or components (e.g., transmitter, receiver, transceiver, and/or other communication circuitry) that perform other functions such as local wireless communications, e.g., with sensor control device 102 under the appropriate protocol (e.g., Wi-Fi, Bluetooth, Bluetooth Low Energy, Near Field Communication (NFC), Radio Frequency Identification (RFID), proprietary protocols, and others) and determining the geographic position of reader device 120 (e.g., global positioning system (GPS) hardware). One or more other antennas 214 are associated with the functional circuitry 212 as needed to operate with the various protocols and circuits.

Power supply 216 can include one or more batteries, which can be rechargeable or single-use disposable batteries. Power management circuitry 218 can regulate battery charging and power supply monitoring, boost power, perform DC conversions, and the like.

Reader device 120 can also include or be integrated with a drug (e.g., insulin, etc.) delivery device such that they, e.g., share a common housing. Examples of such drug delivery devices can include medication pumps having a cannula that remains in the body to allow infusion over a multi-hour or multi-day period (e.g., wearable pumps for the delivery of basal and bolus insulin). Reader device 120, when combined with a medication pump, can include a reservoir to store the drug, a pump connectable to transfer tubing, and an infusion cannula. The pump can force the drug from the reservoir, through the tubing and into the diabetic's body by way of the cannula inserted therein. Other examples of drug delivery devices that can be included with (or integrated with) reader device 120 include portable injection devices that pierce the skin only for each delivery and are subsequently removed (e.g., insulin pens). A reader device 120, when combined with a portable injection device, can include an injection needle, a cartridge for carrying the drug, an interface for controlling the amount of drug to be delivered, and an actuator to cause injection to occur. The device can be used repeatedly until the drug is exhausted, at which point the combined device can be discarded, or the cartridge can be replaced with a new one, at which point the combined device can be reused repeatedly. The needle can be replaced after each injection.

The combined device can function as part of a closed-loop system (e.g., an artificial pancreas system requiring no user intervention to operate) or semi-closed loop system (e.g., an insulin loop system requiring seldom user intervention to operate, such as to confirm changes in dose). For example, the diabetic's analyte level can be monitored in a repeated automatic fashion by sensor control device 102, which can then communicate that monitored analyte level to reader device 120, and the appropriate drug dosage to control the diabetic's analyte level can be automatically determined and subsequently delivered to the diabetic's body. Software instructions for controlling the pump and the amount of insulin delivered can be stored in the memory of reader device 120 and executed by the reader device's processing circuitry. These instructions can also cause calculation of drug delivery amounts and durations (e.g., a bolus infusion and/or a basal infusion profile) based on the analyte level measurements obtained directly or indirectly from sensor control device 102. In some embodiments sensor control device 102 can determine the drug dosage and communicate that to reader device 120.

Example Embodiments of Sensor Control Devices

Figure 1C:
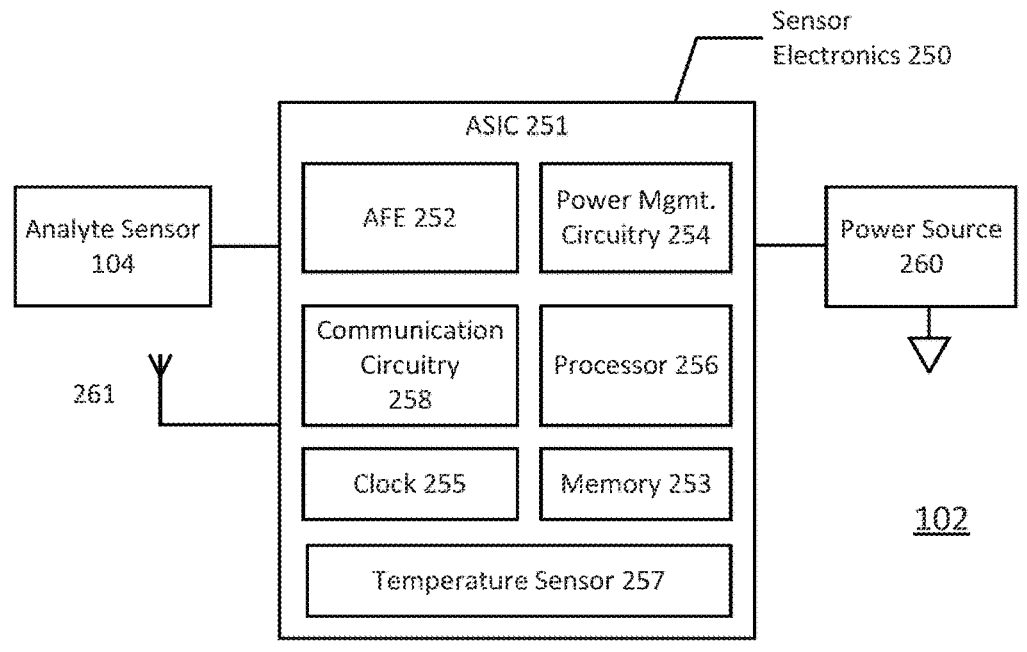
FIG. 1C is a block diagram depicting an example embodiment of sensor control device.

FIG. 1C is a block diagram depicting an example embodiment of sensor control device 102 having analyte sensor 104 and sensor electronics 250 (including analyte monitoring circuitry) that can have the majority of the processing capability for rendering end-result data suitable for display to the user. In FIG. 1C, a single semiconductor chip 251 is depicted that can be a custom application specific integrated circuit (ASIC). Shown within ASIC 251 are certain high-level functional units, including an analog front end (AFE) 252, power management (or control) circuitry 254, processor 256, and communication circuitry 258 (which can be implemented as a transmitter, receiver, transceiver, passive circuit, or otherwise according to the communication protocol). In this embodiment, both AFE 252 and processor 256 are used as analyte monitoring circuitry, but in other embodiments either circuit can perform the analyte monitoring function. Processor 256 can include one or more processors, microprocessors, controllers, and/or microcontrollers, each of which can be a discrete chip or distributed amongst (and a portion of) a number of different chips.

A memory 253 is also included within ASIC 251 and can be shared by the various functional units present within ASIC 251, or can be distributed amongst two or more of them. Memory 253 can also be a separate chip. Memory 253 is non-transitory and can be volatile and/or non-volatile memory. In this embodiment, ASIC 251 is coupled with power source 260, which can be a coin cell battery, or the like. AFE 252 interfaces with in vivo analyte sensor 104 and receives measurement data therefrom and outputs the data to processor 256 in digital form, which in turn can, in some embodiments, process in any of the manners described elsewhere herein. This data can then be provided to communication circuitry 258 for sending, by way of antenna 261, to reader device 120 (not shown), for example, where minimal further processing is needed by the resident software application to display the data. Antenna 261 can be configured according to the needs of the application and communication protocol. Antenna 261 can be, for example, a printed circuit board (PCB) trace antenna, a ceramic antenna, or a discrete metallic antenna. Antenna 261 can be configured as a monopole antenna, a dipole antenna, an F-type antenna, a loop antenna, and others.

Information may be communicated from sensor control device 102 to a second device (e.g., reader device 120) at the initiative of sensor control device 102 or reader device 120. For example, information can be communicated automatically and/or repeatedly (e.g., continuously) by sensor control device 102 when the analyte information is available, or according to a schedule (e.g., about every 1 minute, about every 5 minutes, about every 10 minutes, or the like), in which case the information can be stored or logged in a memory of sensor control device 102 for later communication. The information can be transmitted from sensor control device 102 in response to receipt of a request by the second device. This request can be an automated request, e.g., a request transmitted by the second device according to a schedule, or can be a request generated at the initiative of a user (e.g., an ad hoc or manual request). In some embodiments, a manual request for data is referred to as a "scan" of sensor control device 102 or an "on-demand" data transfer from device 102. In some embodiments, the second device can transmit a polling signal or data packet to sensor control device 102, and device 102 can treat each poll (or polls occurring at certain time intervals) as a request for data and, if data is available, then can transmit such data to the second device. In many embodiments, the communication between sensor control device 102 and the second device are secure (e.g., encrypted and/or between authenticated devices), but in some embodiments the data can be transmitted from sensor control device 102 in an unsecured manner, e.g., as a broadcast to all listening devices in range.

Different types and/or forms and/or amounts of information may be sent as part of each communication including, but not limited to, one or more of current sensor measurements (e.g., the most recently obtained analyte level information temporally corresponding to the time the reading is initiated), rate of change of the measured metric over a predetermined time period, rate of the rate of change of the metric (acceleration in the rate of change), or historical metric information corresponding to metric information obtained prior to a given reading and stored in a memory of sensor control device 102.

Some or all of real time, historical, rate of change, rate of rate of change (such as acceleration or deceleration) information may be sent to reader device 120 in a given communication or transmission. In certain embodiments, the type and/or form and/or amount of information sent to reader device 120 may be preprogrammed and/or unchangeable (e.g., preset at manufacturing), or may not be preprogrammed and/or unchangeable so that it may be selectable and/or changeable in the field one or more times (e.g., by activating a switch of the system, etc.). Accordingly, in certain embodiments reader device 120 can output a current (real time) sensor-derived analyte value (e.g., in numerical format), a current rate of analyte change (e.g., in the form of an analyte rate indicator such as an arrow pointing in a direction to indicate the current rate), and analyte trend history data based on sensor readings acquired by and stored in memory of sensor control device 102 (e.g., in the form of a graphical trace). Additionally, an on-skin or sensor temperature reading or measurement may be collected by an optional temperature sensor 257. Those readings or measurements can be communicated (either individually or as an aggregated measurement over time) from sensor control device 102 to another device (e.g., reader 120). The temperature reading or measurement, however, may be used in conjunction with a software routine executed by reader device 120 to correct or compensate the analyte measurement output to the user, instead of or in addition to actually displaying the temperature measurement to the user.

Example Embodiments of Calibration

Analyte sensors can be described by one or more sensing characteristics. A common sensing characteristic is referred to as the analyte sensor's sensitivity, which is a measure of the sensor's responsiveness to the concentration of the chemical or composition it is designed to detect. For electrochemical sensors, this response can be in the form of an electrical current (amperometric) or electrical charge (coulometric). For other types of sensors, the response can be in a different form, such as a photonic intensity (e.g., optical light). The sensitivity of an analyte sensor can vary depending on a number of factors, including whether the sensor is in an in vitro state or an in vivo state.

Figure 2A:
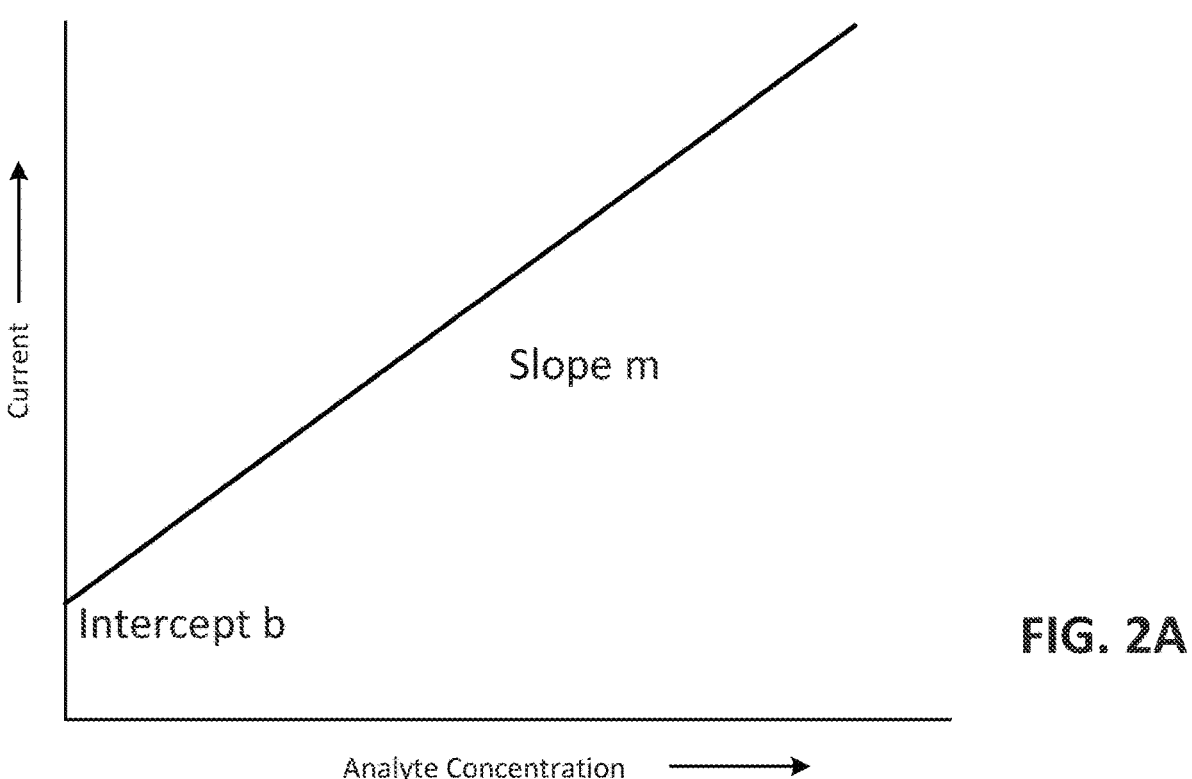
FIG. 2A is a graph depicting an example of an in vitro sensitivity of an analyte sensor.

FIG. 2A is a graph depicting the in vitro sensitivity of an amperometric analyte sensor. The in vitro sensitivity can be obtained by in vitro testing the sensor at various analyte concentrations and then performing a regression (e.g., linear or non-linear) or other curve fitting on the resulting data. In this example, the analyte sensor's sensitivity is linear, or substantially linear, and can be modeled according to the equation y=mx+b, where y is the sensor's electrical output current, x is the analyte level (or concentration), m is the slope of the sensitivity and b is the intercept of the sensitivity, where the intercept generally corresponds to a background signal (e.g., noise). For sensors with a linear or substantially linear response, the analyte level that corresponds to a given current can be determined from the slope and intercept of the sensitivity. Sensors with a non-linear sensitivity require additional information to determine the analyte level resulting from the sensor's output current, and those of ordinary skill in the art are familiar with manners by which to model non-linear sensitivities. In certain embodiments of in vivo sensors, the in vitro sensitivity may be the same as the in vivo sensitivity, but in other embodiments a transfer (or conversion) function is used to translate the in vitro sensitivity into the in vivo sensitivity that is applicable to the sensor's intended in vivo use.

Figure 2B:
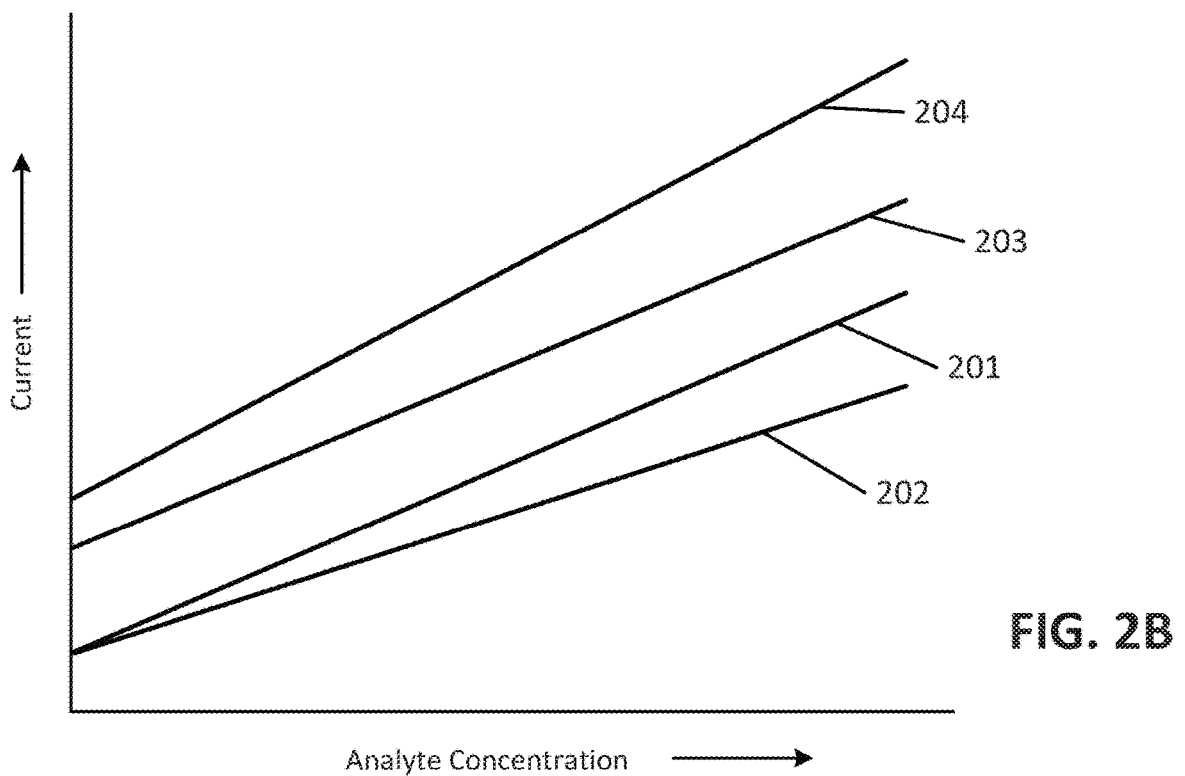
FIG. 2B is a graph depicting examples of different sensitivities for analyte sensors.

Analyte sensors of the same design undergoing the same manufacturing process can have different in vitro sensitivities (as well as in vivo sensitivities, if applicable) due to variations in that manufacturing process and the materials used for fabrication. FIG. 2B depicts examples of different sensitivities 201-204 for different analyte sensors of the same mechanical and electrochemical design. The sensitivities 201-204 in this example are linear for ease of illustration, but in other examples can be non-linear. Here, a first sensitivity 201 has the same intercept as a second sensitivity 202, but a greater slope. A third sensitivity 203 has generally the same slope as that of sensitivity 201, but a greater intercept. A fourth sensitivity 204 has a still greater slope and intercept that those of sensitivities 201-203.

In order to compensate for these variations, the sensor can be calibrated. Calibration is a technique for improving or maintaining accuracy by adjusting a sensor's measured output to reduce the differences with the sensor's expected output. One or more parameters that describe the sensor's sensing characteristics, like its sensitivity, are established for use in the calibration adjustment.

After using an in vivo sensor to obtain a raw measurement signal from the user's body, the on body electronics can apply analog signal conditioning to the raw signal and convert the signal into a digital form of the conditioned raw signal. For example, the digital raw data can be in counts converted by an A/D converter from the raw analog signal (for example, voltage or amps). In some embodiments, this conditioned raw digital data can be encoded for transmission to another device, e.g., a reader device as described herein, which then algorithmically processes that digital raw data into a processed result representative of the user's analyte level (e.g., a result readily made suitable for display to the user). This algorithmic processing utilizes the calibration information for the sensor to arrive at the processed result, and can utilize other one or more other variables depending upon the implementation. This algorithmically processed result can then be digitally formatted or graphically processed for digital display to the user. In other embodiments, the on body electronics itself can algorithmically process the digital raw data into the processed result that is representative of the user's measured analyte level, and then encode and wirelessly communicate that data to a reader device, which in turn can format or graphically process the received data for digital display to the user. In some such embodiments, the on body electronics can further graphically process the processed result of the data such that it is ready for display, and then display that data on a display of on body electronics or transmit the data to a display device. In some embodiments, the processed analyte data result (prior to graphic processing) is used by the system (e.g., incorporated into a diabetes monitoring regime) without processing for display to the user. In some embodiments, the on body electronics and/or the display device transmit the digital raw data to another computer system for algorithmic processing and display.

Certain embodiments of in vivo analyte monitoring systems require calibration to occur after implantation of the sensor into the user or patient, either by user interaction or by the system itself in an automated fashion. For example, when user interaction is required, the user performs an in vitro measurement (e.g., a blood glucose (BG) measurement using a finger stick and an in vitro test strip) and enters this into the system, while the analyte sensor is implanted. The system then compares the in vitro measurement with the in vivo signal and, using the differential, determines an estimate of the sensor's in vivo sensitivity. The in vivo sensitivity can then be used in an algorithmic process to transform the data collected with the sensor to a value that indicates the user's analyte level. This and other processes that require a user to make an in vitro reference measurement to perform calibration are referred to as "user calibration." Multiple user calibrations (e.g., according to a periodic (e.g., daily) schedule or on an as-needed basis) may be required to maintain accuracy. While the embodiments described herein can incorporate a degree of user calibration for a particular implementation, generally this is not preferred as it requires the user to perform a painful or otherwise burdensome BG measurement, and can introduce user error.

Some embodiments of in vivo analyte monitoring systems operate with a sensor that is factory calibrated. Factory calibration refers to the determination or estimation of the one or more calibration parameters prior to distribution to the user or healthcare professional (HCP). The calibration parameter can be determined by the sensor manufacturer (or the manufacturer of the other components of the sensor control device if the two entities are different).

Factory calibration can be implemented with user calibration or without any user calibration. For example, in all of the embodiments described herein, the in vivo sensors can be calibrated by the manufacturer and then provided to the user, who can then use such sensors for the duration of their lifespan to accurately monitor the user's in vivo analyte levels, and no step of user calibration is performed during that lifespan. Such systems and methods determine clinically accurate analyte concentrations at least over the predetermined sensing period of analyte sensor systems without obtaining one or more independent analyte measurements (e.g., without using an in vitro test strip or other reference device) for calibration of a generated analyte related signal from the analyte sensor during the usage life of the sensor. In other words, once the analyte sensors are positioned in the body of the user, control logic or microprocessors in the sensor electronics, or the microprocessors in the display device include one or more algorithms or programming to accurately convert or correlate signals related to the sensed analyte (e.g., in nanoamps (nA), counts, or other appropriate units) to a corresponding analyte level (e.g., converted to an analyte level in milligrams per deciliter (mg/dL) or other appropriate units) without a reference value provided to the system, rendering sensor calibration "invisible" to the user such that the system does not require any human intervention for analyte sensor calibration.

The calibration information can be in the form of one or more calibration parameters, or one or more calibration codes, that can be stored in the memory of the corresponding sensor control device, such that when a user initiates operation of the sensor control device, the requisite calibration information is readily available. In some cases, the calibration information is made available to the user (e.g., such as a sensor code printed on packaging, etc.) and then manually input (or input using a scanner, e.g., optical or magnetic)) into the reader or sensor control device.

Example Embodiments of Duration-Based Adjustment of Sensor Signals

The calibration information is representative of an attempt to accurately model the sensor's response or sensitivity. In certain analyte monitoring systems 100 however, the sensitivity of sensor 101 can change over time after sensor 101 is initially manufactured. This can be caused by a number of factors, including environmental exposure (e.g., temperature, humidity, air pressure), the duration of time the sensors are in existence post-manufacture and prior to use, or the duration of time the sensors are in use post-manufacture. These variations can cause sensors of the same design and manufacturing process to have measurable differences in their performance. If the sensor sensitivity changes and this change is not compensated for, such as by adjusting the calibration information, then the resulting analyte data will not be as accurate. The algorithmic scaling process performed on the data obtained from the sensor will result in analyte concentrations that deviate from those actually present.

The relevant time periods occurring post-manufacture can be referred to as the "shelf duration" and the "wear duration." Shelf duration generally refers to the time period after manufacture and before use of the sensor, during which the sensor is generally in a packaged state. Wear duration generally refers to the time period during which the sensor is used by the user, which in the case of in vivo sensor 101 is generally the time that the sensor is at least partially implanted within the body of the user.

Example embodiments described herein can compensate for a change in sensor response due to the length of shelf duration in order to achieve and maintain a higher degree of accuracy than without such compensation, which results in improved overall performance. In addition, or alternatively, example embodiments described herein can compensate for a change in sensor response due to the length of wear duration, in order to achieve and maintain a higher degree of accuracy than without such compensation, also resulting in improved overall performance.

The compensation can be applied by processing circuitry executing software instructions, where this processing circuitry is within sensor control device 102, reader device 120, computer system 170, or elsewhere in system 100. This compensation can occur in the same stage of processing where sensor-derived data is adjusted with the calibration information, but is not limited to such, and can occur at any processing stage where analyte data is manipulated.

For ease of description, the compensation embodiments will be described in the context of a sensor 101 modeled with a linear sensitivity having a slope and offset. However, the embodiments described herein are not limited to such, and can also be applied to sensors modeled with two or more linear sensitivities (e.g., for regions of different measurement magnitudes), one or more nonlinear sensitivities, or any combination thereof.

An example of a linear equation that converts or adjusts a first analyte value (G_init) to a second, calibrated value (G_cal) is as follows:

$$G\_cal = G0 + \left[ \frac{G\_init}{Sc} \right] \tag{1}$$

where G0 and Sc are the offset (e.g., intercept) and the slope, respectively, of the linear sensitivity associated with a particular sensor, or group of sensors (e.g., in a sensor production lot). In some embodiments, the parameters G0 and Sc can be functions of other pre-determined parameters STI and STS associated with a particular sensor or group of sensors, e.g., G0=−STI/STS and Sc=STS. The values of G0 and Sc, or other pre-determined parameters, can be provided to sensor control device 102 (or other devices in system 100) as a code (as discussed elsewhere herein). In some embodiments, these parameters are used over the lifetime of the sensor without modification. In other embodiments, at least one of G0 and Sc is modified one or more times with a user calibration, e.g., based on the results of a finger stick measurement made by the user. For clarity, it is noted that the embodiments described herein can be accomplished using only factory calibration, only user calibration, a combination of factory and user calibration, or otherwise.

G_init can any initial or intermediate analyte data value to which calibration is applied. For example, G_init can be a raw value that has not undergone any processing in the digital domain (e.g., representative of the counts from an analog-digital converter), or G_init can be a processed value that has been algorithmically adjusted in the digital domain but that still requires some calibration scaling. G_cal can be a final processed value, e.g., ready for output to the user, or can be subjected to further algorithmic processing for other purposes.

In many example embodiments, the equation (1) can be modified to account for shelf duration and/or wear duration. For example, a modified form of (1) that accounts for both shelf duration and wear duration is as follows:

$$G0 = \left[ \frac{-STI}{STS} \right] + f\_gWear + f\_gShelf \tag{2}$$

$$Sc = STS \times [1 + f\_sWear + f\_sShelf] \tag{3}$$

where the functions f_gWear and f_sWear are G0 and Sc adjustments, respectively, to account for wear duration, and the functions f_gShelf and f_sShelf are G0 and Sc adjustments, respectively, to account for shelf duration. In certain embodiments, each of the adjustments can be a function of time:

$$f\_gWear = K\_G0\_wear \times T\_wear \tag{4}$$

-continued $$f\_sWear = R\_Sc\_wear \times T\_wear \qquad (5)$$

$$f\_gShelf = K\_G0\_shelf \times T\_shelf \qquad (6)$$

$$f\_sShelf = R\_Sc\_shelf \times T\_shelf \qquad (7)$$

where T_wear is the wear duration and T_shelf is the shelf duration, where K_G0_wear, R_Sc_wear are constant or variable parameters that provide adjustment to G0 and Sc for wear duration, and where K_G0_shelf and R_Sc_shelf are constant or variable parameters that provide adjustment to G0 and Sc for shelf duration. The functions f_gWear and f_gShelf can operate in the same units of analyte concentration as G0 and G_cal. The functions f_sWear and f_sShelf can operate in the same units of the reciprocal of slope, 1/Sc.

In yet another embodiment, the adjustment for offset G0 over time can be a pair of functions that modify only the pre-determined parameter STI instead:

$$G0 = [-STGI + f\_iWear + f\_iShelf] / STS \qquad (2a)$$

Where the functions f_iWear and f_iShelf are similar to f_gWear and f_gShelf, respectively, but vary in the appropriate units scaled by STS relative to each other. For ease of discussion, many embodiments discussed below assume the use of equation (2) and not equation (2a), although those embodiments can by implemented using either equation (2) or (2a), or others.

In the embodiments described herein, system 100 can adjust for both wear duration and shelf duration as in example equations (2) and (3). However, the embodiments described herein can account for just wear duration if desired. In such embodiments, for example, only the terms f_gWear and f_sWear are included in equations (2) and (3), and the terms f_gShelf and f_sShelf are omitted. Conversely, the embodiments described herein can account for just wear duration if desired. In such embodiments, for example, only the terms f_gShelf and f_sShelf are included in equations (2) and (3), and the terms f_gWear and f_sWear are omitted.

Similarly, the embodiments of system 100 can adjust one or both of G0 and Sc. For example, in certain embodiments, sensor 101 may only exhibit duration-based sensitivity change for G0, in which case equation (2) can be implemented with equation (1) but Sc remains equal to STS. Further, if only one of wear duration or shelf duration is compensated for G0, then then only that corresponding function (f_gWear, f_gShelf) can be included in equation (2). In other embodiments, sensor 101 may only exhibit duration-based sensitivity change for Sc, in which case equation (3) can be implemented with equation (1) but G0=−STI/STS. Further, if only one of wear duration or shelf duration is compensated for Sc, then then only that corresponding function (f_sWear, f_sShelf) can be included in equation (2).

T_wear and T_shelf can be expressed in units of time (e.g., seconds, minutes, hours, days, weeks, months, etc.) or any other units that are representative of a particular duration (e.g., such as counts on a counter). T_wear is preferably representative of the amount or duration of time the sensor is in an in vivo state. T_shelf is preferably representative of the amount or duration of time that transpired between completion of the sensor's manufacture (shelf start time) and insertion of the sensor into the user's body (shelf stop time).

There are various ways these durations can be measured, depending on what actions constitute the start and stop times, and these variations are discussed further below.

K__G0_wear, R_Sc_wear, K_G0_shelf, and R_Sc_shelf can be determined theoretically and/or empirically. In some embodiments, K_G0_wear and R_Sc_wear are determined empirically, e.g., through in vitro testing of sensors over time, in vivo testing of sensors over time, and/or a combination thereof, to assess the characteristics of the sensitivity change occurring while the sensor is being used in vivo. Values for K_G0_wear and R_Sc_wear can then be extrapolated from the resulting data set, e.g., through regression or curve-fitting analysis, and used as the parameters for other sensors. In other embodiments, values for K_G0_wear and R_Sc_wear can be determined from a theoretical model that models sensor performance in vivo. In still other embodiments, values for K_G0_wear and R_Sc_wear can be determined from both empirical data and a theoretical model.

In some embodiments, K_G0_shelf and R_Sc_shelf are determined empirically, e.g., through in vitro or in vivo testing of sensors that have been subjected to differing amounts of shelf durations, and/or a combination thereof, to assess the characteristics of the sensitivity change occurring while the sensor is in storage. Values for K_G0_shelf and R_Sc_shelf can then be extrapolated from the resulting data set, e.g., through regression or curve-fitting analysis, and used as the parameters for other sensors. In other embodiments, values for K_G0_shelf and R_Sc_shelf can be determined from a theoretical model that models sensor sensitivity changes over time while ex vivo. In still other embodiments, values for K_G0_shelf and R_Sc_shelf can be determined from both empirical data and a theoretical model.

Depending on a variety of factors, including the degree of variation in K_G0_wear, R_Sc_wear, K_G0_shelf, and R_Sc_shelf, in some embodiments one set of these parameters can be determined and applied to an entire production line of sensors (e.g., across hundreds or thousands of production lots). In other embodiments, these parameters can be determined and applied for different groups or subsets of sensors within the production line, e.g., these parameters can be determined separately for each lot of sensors being manufactured, and applied only to those sensors in that lot.

Before performing functions (4)-(7), in many embodiments T_wear and/or T_shelf are first converted into a scaling factor without units, for example, an integer or decimal value. The conversion can be linear or nonlinear, or otherwise as described in further detail herein. T_wear and T_shelf can be determined each time a calibration is performed, or T_wear and T_shelf can be determined at regular or irregular intervals that have a lower frequency than the frequency at which calibrations are performed. For example, if calculation of analyte values such as G_cal is performed once per minute, T_wear can also be determined once per minute, or at a lower frequency (e.g., once per ten minutes, once per hour, etc.), depending on the needs of the particular implementation. T_shelf can be determined once and then used for all subsequent calibrations, which is efficient, since T_shelf will often be constant once in vivo sensor use has begun.

Figure 3A:
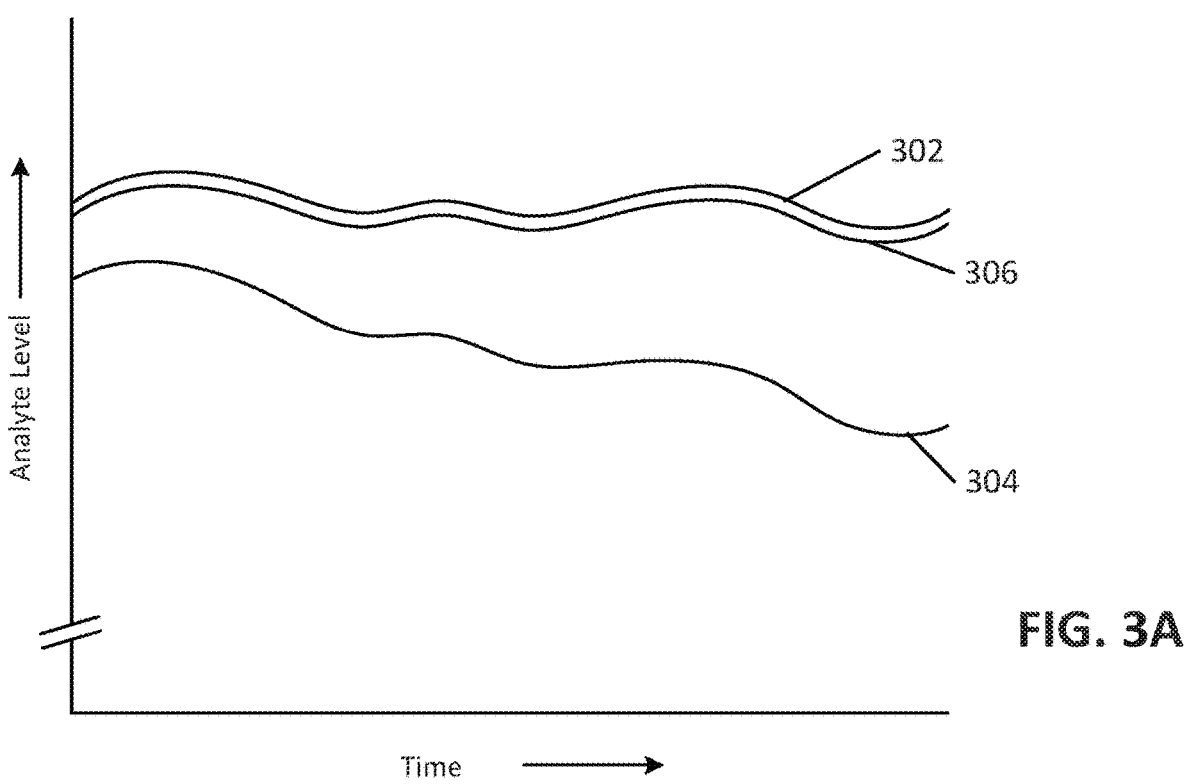
FIG. 3A is a graph depicting example traces corresponding to actual analyte levels, analyte levels determined from data not compensated for wear duration, and analyte levels determined from data compensated for wear duration.

FIG. 3A is graph depicting an example adjustment to sensor data for wear duration. The y-axis represents measured in vivo analyte levels (e.g., G_cal) and the x-axis represents time. Trace 302 represents actual analyte levels over time for a user, and trace 304 represents average analyte levels collected from a sensor 101 for that user over time where no wear duration adjustment has been performed.

(Any effects of in vivo sensor lag are ignored for ease of illustration.) Here, trace 304 exhibits generally lower values than the actual values of trace 302 due to a change in in vivo sensitivity over the duration of wear. Trace 306 represents the analyte levels of trace 304 after wear duration calibration has been performed according to the embodiments herein. As can be seen, application of wear duration calibration can adjust the values of trace 304 such that they more closely approximate the actual analyte levels of the user.

Figure 3B:
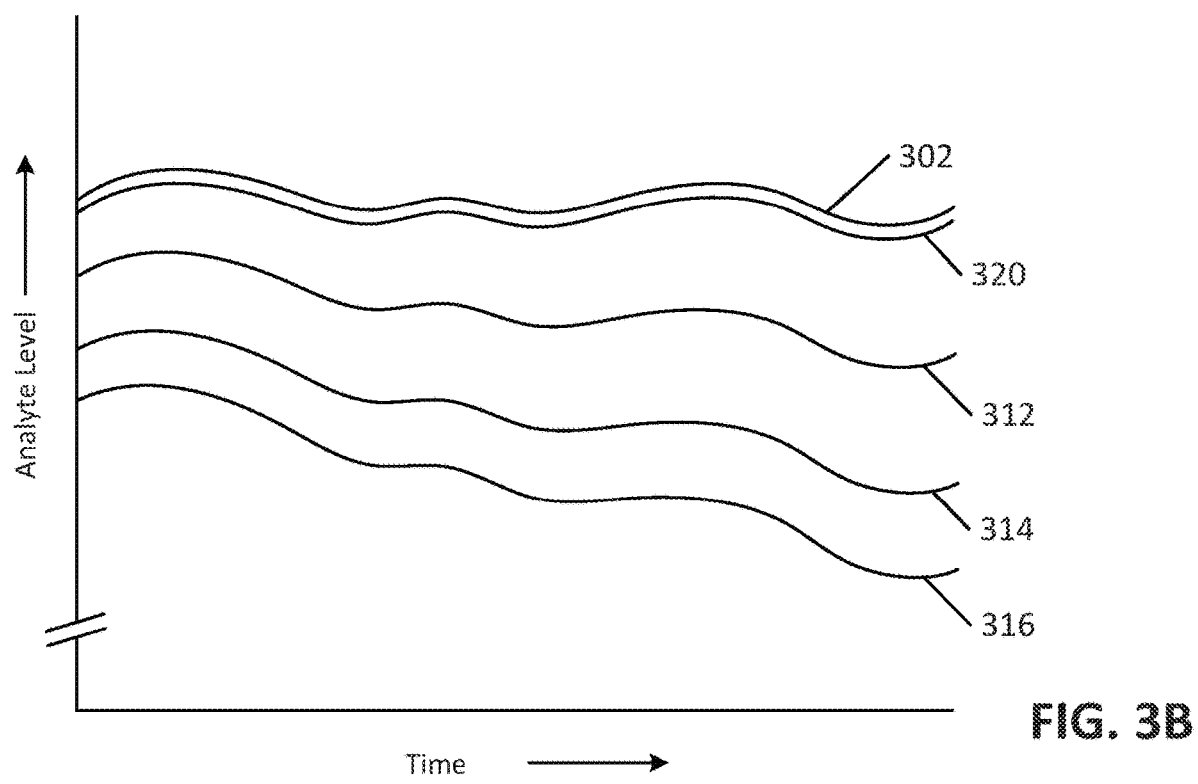
FIG. 3B is a graph depicting example traces corresponding to actual analyte levels, analyte levels determined from various sensors not compensated for shelf duration, and analyte levels determined from data compensated for shelf duration.

FIG. 3B is graph depicting an example adjustment to sensor data for shelf duration. The y-axis represents measured in vivo analyte levels (e.g., G_cal) and the x-axis represents time. Trace 302 represents actual analyte levels over time for a user. Traces 312, 314, and 316 represent average analyte levels collected from the user with three different sensors 101 over the same period of time where no shelf duration adjustment has been performed. (Any effects of in vivo sensor lag are ignored for ease of illustration.) Here, trace 312 was derived from a sensor 101 having a first shelf duration (A), trace 314 was derived from a sensor 101 having a second shelf duration (B), and trace 316 was derived from a sensor 101 having a third shelf duration (C), where C is greater than B, which is greater than A (C>B>A). Trace 320 represents the analyte levels of traces 312-316 after shelf duration calibration has been performed according to the embodiments herein. As can be seen, application of shelf duration calibration can adjust the values of traces 312-316 such that they more closely approximate the actual analyte levels of the user. Here, traces 312-316 have been adjusted to the same values 320, although in some actual implementations the adjusted forms of traces 312-316 may be different from each other, although still more closely approximating the actual analyte levels of trace 302. In some implementations, trace 320 and any other adjusted values align directly with trace 302.

Additional Examples of Determining Shelf Duration

There are various ways shelf duration (T_shelf) can be determined, depending on what actions constitute the start and stop times. For example, the T_shelf start time can be the time at which the sensor: completed manufacturing, completed testing, completed final assembly into sensor control device 102, completed the packaging procedure, or others. In many embodiments, the T_shelf start time can be stored in memory of sensor control device 102 at the time of manufacture or packing, such as in the form of a time and/or date stamp of manufacture. The T_shelf start time can be input to the memory using a wired or wireless communication link. In some embodiments, the T_shelf start time is linked to an identifier of the sensor (e.g., a unique serial number), and that identifier is communicated over an internet connection to a server (e.g., trusted computer system 180), which then provides the corresponding T-shelf start time for that sensor to the appropriate component of system 100 (e.g., sensor control device 102 or reader 120) making the T_shelf determination. In some embodiments, the T_shelf start time is printed on the packaging of the sensor 101 or sensor control device 102, and the user can input the T_shelf start time into the appropriate component of system 100. Various methods of user input of the T_shelf start time include manually keying the start time into system 100, reading the start time with an optical scanner (e.g., camera photo of alphanumeric code in combination with optical character recognition (OCR), camera photo of 2D or 3D barcode, etc.), wireless scanning (e.g., reading an RFID or NFC tag with reader 120), reading with a ROM calibrator, or others.

Similarly, the T_shelf stop time can be determined in various ways. For example, the T_shelf stop time can be the time at which sensor 101 is inserted into the patient's body, the time at which sensor control unit 102 is activated, the time a first measured analyte value is collected from sensor 101 from the user's body, the time a first analyte level collected from sensor 101 (in an in vivo state) is displayed to the user on reader device 120, or others. The clock used to determine the stop time of T_shelf can be determined from a present time supplied to system 100, e.g., a network clock provided to a smart phone reader 120 by a mobile telephone network, or a time tracked or maintained by system 100, e.g., a time entered into system 100 by the user (e.g., by a set time function) and then maintained by an internal clock, or the like.

Software instructions for determining the shelf start time and/or shelf stop time can be stored on the appropriate device (e.g., sensor control device 102 or reader device 120), which can execute those instructions with processing circuitry and record the respective start and/or stop times when they occur, store them in memory, and/or communicate them to other devices within system 100.

The devices within system 100 can determine T_shelf by subtracting the start time from the stop time. This may involve communication of the start time and/or stop time from one device in system 100 to another (e.g., between sensor control device 102 and reader device 120). In one embodiment, sensor control device 102 has the T_shelf start time in memory and determines the T_shelf stop time, and then subtracts the T_shelf start time from the T_shelf stop time to determine T_shelf, which is then used by sensor control device 102 to calibrate the analyte signals. In another embodiment, sensor control device 102 communicates the shelf start and stop times to reader device 120 which then determines T_shelf and performs the calibration. In another embodiment, sensor control device 102 determines T_shelf and communicates it to reader device 120, which then performs the calibration. In another embodiment, sensor control device 102 communicates the start time to reader device 120, which determines the stop time, then determines T_shelf and then performs the calibration. In yet another embodiment, the start time is provided to reader device 120 in another manner (e.g., by user input to reader device 120, by communication to reader device 120 over the internet from a server), and reader device 120 then determines the stop time, then determines T_shelf, and then performs the calibration. In still another embodiment, sensor control device 102 and/or reader device 120 communicate with a server (e.g., trusted computer system 180), which determines T_shelf and communicates it over the internet to the appropriate device(s) in system 100 (e.g., sensor control device 102 and/or reader device 120).

In some embodiments, a clock, counter, or other timer is started at the start time and operated (e.g., repeatedly incremented) to the stop time, and the final output of that clock is used to determine T_shelf. Such a clock could be located within sensor control device 102, or could be maintained on a network, the output of which is then provided to the appropriate device of system 100.

In the embodiments described herein, system 100 can be programmed to wait for a period of time (e.g., a wait period) before setting the T_shelf start time, or to automatically deduct this period of time from the shelf duration, or to otherwise determine T_shelf such that it is reduced by the wait period. For example, the calculation of T_shelf may start after the T_shelf wait period has elapsed. The T_shelf wait period can be, for example, a certain number of minutes, hours, days, weeks, or months, etc. For example, the T_shelf wait period can be a certain time period after completion of sensor manufacture, or sensor control device 102 packaging, etc. The value of this wait period can be pre-determined and stored in memory (e.g., of sensor control device 102 or reader 120), or can be coded directly within the software instructions of the respective device, such that the analyte processing algorithm has access to it. In other embodiments, the value of the wait period can be communicated to the appropriate device in system 100 at the time of initial use or activation of sensor control device 102 (e.g., by sending the wait period value to reader 120 over the internet).

In embodiments where T_shelf start is delayed by the wait period, then T_shelf can then be determined by subtracting the start time from the stop time. In other embodiments, the delayed shelf start time can be determined by adding the wait period duration to the original start time (e.g., completion of manufacturing or packaging). In other embodiments, the shelf duration is determined by subtracting both the original start time and the wait period from the stop time. In still other embodiments, the shelf start time is stored (e.g., by a device of system 100) as the original time incremented by the wait period, such that determination of T_shelf can be accomplished by subtracting this incremented time from the shelf stop time. In embodiments that use an active clock, counter, or timer to track shelf duration, this clock, counter, or timer can be incremented by the wait period.

In some embodiments, the length or magnitude of the wait period can be stored as an enumeration or code, which can then be translated into a length of time. For example, sensor control device 102 can store the wait period as one or more bits, which can then be referenced against a key or look-up table to determine the corresponding length of time (e.g., a two-bit number can be converted into a period of zero time, one or more minutes, one or more hours, one or more days, one or more weeks, etc.).

Additional Examples of Determining Wear Duration

Like shelf duration, there are various ways wear duration (T_wear) can be determined, depending on what actions constitute the wear start time and current time. System 100 can, in some embodiments, determine T_wear by subtracting a T_wear start time from a current time (or wear current time, which is the time used to approximate the current time).

For example, the T_wear start time can be the time of insertion of sensor 101 into the body of the patient or user, the time since activation of the sensor control unit 102 with the sensor 101 implanted within the user's body, the time since a first measured analyte value was collected from sensor 101 from the user's body, the time since a first analyte level collected from sensor 101 (in an in vivo state) was displayed to the user on reader device 120, and so forth. In some embodiments, software instructions executed by the processing circuitry of a device in system 100 (e.g., sensor control device 102, reader device 120, etc.) can determined the wear start time automatically. In other embodiments, the user can manually input the wear start time into the device of system 100 (e.g., by input with a touchscreen or keypad of reader 120). In other embodiments, the device of system 100 can prompt the user if the start time is the current time (or a particular time recently transpired), and upon confirmation can use that time as the start time.

Determine of T_wear by subtracting the wear start time from the wear current time may involve communication of the wear start time and/or wear current time from one device in system 100 to another (e.g., between sensor control device

102 and reader device 120). In one embodiment, sensor control device 102 has the T_wear start time in memory and determines the T_wear current time, and then subtracts the T_wear start time from the T_wear current time to determine T_wear, which is then used by sensor control device 102 to calibrate the analyte signals. In another embodiment, sensor control device 102 communicates the wear start and current times to reader device 120 which then determines T_wear and performs the calibration. In another embodiment, sensor control device 102 determines T_wear and communicates it to reader device 120, which then performs the calibration. In another embodiment, sensor control device 102 communicates the wear start time to reader device 120, which determines the wear current time, then determines T_wear and performs the calibration. In yet another embodiment, the wear start time is provided to reader device 120 in another manner (e.g., by user input to reader device 120, by communication to reader device 120 over the internet from a server), and reader device 120 then determines the wear current time, then determines T_wear, and then performs the calibration. In still another embodiment, sensor control device 102 and/or reader device 120 communicate with a server (e.g., trusted computer system 180), which determines T_wear and communicates it over the internet to the appropriate device(s) in system 100 (e.g., sensor control device 102 and/or reader device 120). In still yet another embodiment, reader device 120 determines the wear start time, and the wear current time, and determines T_wear and then performs the calibration.

The T_wear current time can be determined in various ways. For example, the T_wear current time can be the current time maintained by system 100, or the device in system 100 performing the T_wear calculation. The current time can be provided by a network clock, e.g., a clock provided to a smart phone reader 120 by a mobile telephony network. The current time can be tracked or maintained by a local clock within system 100, e.g., a time entered into system 100 by the user (e.g., by a set time function) or by another source and then maintained by an internal clock, or the like, present in one of the devices of system 100 (e.g., a clock of sensor control device 102, a clock of reader 120, etc.). The wear current time can be approximated depending on the desired degree of accuracy, e.g., multiple analyte measurements taken in relatively quick succession can be adjusted with the same current time.

Instead of tracking the wear start times and wear current time and then calculating the difference, in the embodiments described herein T_wear can be determined by use of a clock, counter, or other timer that is initiated at the wear start time or that otherwise represents the time since the wear start time. The present value of that clock, counter, or timer is representative of T_wear and can be used directly. Such a timing device could be located within sensor control device 102, reader device 120, or could be maintained on a network such that the output of which is then provided to the appropriate device of system 100.

Software instructions for determining the wear start time and/or wear current time can be stored on the appropriate device (e.g., sensor control device 102 or reader device 120), which can execute those instructions with processing circuitry and record the respective start and/or current times when they occur, store them in memory, and/or communicate them to other devices within system 100.

In the embodiments described herein, system 100 can be programmed to wait for a period of time (e.g., a wait period) before setting the T_wear start time, or to automatically deduct this period of time from the wear duration, or to otherwise determine T_wear such that it is reduced by the wait period. For example, the calculation of T_wear may start after the T_wear wait period has elapsed. The T_wear wait period can be, for example, a certain number of seconds, minutes, hours, or days, or weeks, etc. For example, the T_wear wait period can be a certain time period after insertion of sensor 101 into the body, or activation of the electronics of sensor control device 102, etc. The value of this wait period can be pre-determined and stored in memory (e.g., of sensor control device 102 or reader 120), or can be coded directly within the software instructions of the respective device, such that the analyte processing algorithm has access to it. In other embodiments, the value of the wait period can be communicated to the appropriate device in system 100 at the time of initial use or activation of sensor control device 102 (e.g., by sending the wait period value to reader 120 over the internet).

In embodiments where T_wear start is delayed by the wait period, then T_wear can then be determined by subtracting the wear start time from the wear current time. In other embodiments, the delayed wear start time can be determined by adding the wait period duration to the original wear start time (e.g., insertion or activation). In other embodiments, the wear duration is determined by subtracting both the original start time and the wait period from the current wear time. In still other embodiments, the wear start time is stored (e.g., by a device of system 100) as the original time incremented by the wear wait period, such that determination of T_wear can be accomplished by subtracting this incremented time from the wear current time, where negative values can be treated as no adjustment since the wait period has not yet passed. In embodiments that use an active clock or timer to track wear duration, this clock or timer can be incremented by the wait period.

In some embodiments, the length or magnitude of the wear wait period can be stored as an enumeration or code, which can then be translated into a length of time. For example, sensor control device 102 can store the wait period as one or more bits, which can then be referenced against a key or look-up table to determine the corresponding length of time (e.g., a two-bit number can be converted into a period of zero time, one or more minutes, one or more hours, one or more days, one or more weeks, etc.).

Example Embodiments With Time Limitations and/or Time Delineations

In some example embodiments, the adjustment functions themselves (e.g., f_gWear, f_sWear, f_gShelf, f_sShelf, f_iWear, and f_iShelf) can vary. For example, the adjustment functions can have predetermined minimum and/or maximum limits that can be incorporated into the algorithms (and stored in the respective device, e.g., sensor control device 102 or reader 120). The minimum value can be zero or a number greater than zero. For example, regardless of how low the value of T_shelf is, the functions f_gShelf and f_sShelf will not be below a set minimum value, and regardless of how high the value of T_shelf is, the functions f_gShelf and f_sShelf will not exceed a set maximum value. The set minimum and maximum values for each of the functions f_gShelf and f_sShelf can differ. Similarly, for example, regardless of how low the value of T_wear is, the functions f_gWear and f_sWear will not be below a set minimum value, and regardless of how high the value of T_wear is, the functions f_gWear and f_sWear will not exceed a set maximum value. The set minimum and maximum values for each of the functions f_gWear and f_sWear can differ. For example, in one embodiment, f_gWear is as follows:

$$f\_gWear = G\_w1 \text{ for } T\_wear \text{ less than or equal to } T\_w1 \text{ days;} \quad (8)$$

$$f\_gWear =$$
$$G\_w1 + [(t - T\_w1) * (G\_w2 - G\_w1) / (T\_w2 - T\_w1)] \text{ for}$$
$$T\_wear \text{ greater than } T\_w1$$
$$\text{days and less than or equal to } T\_w2 \text{ days; and}$$
$$f\_gWear = G\_w2 \text{ for } T\_wear \text{ greater than } T\_w2 \text{ days,}$$

where G_w1 is a minimum constant, G_w2 is a maximum constant, and t is the current wear duration.

In some example embodiments, different adjustment functions (f_gWear, f_sWear, f_gShelf, and f_sShelf) can be used dependent on the magnitude of the respective duration. For example, with respect to wear duration, if T_wear is below a first value, then a first version of f_gWear and a first version of f_sWear can be used and, if T_wear is above the first value, then a second version of f_gWear and a second version of f_sWear can be used (which can be extended for T_wear being above a second value, a third value, and so on). Each of the different versions can be a constant value or a variable function (e.g., a linear or nonlinear equation).

In other embodiments, the adjustment functions (e.g., f_gWear, f_sWear, f_gShelf, f_sShelf, f_iWear, and f_iShelf) can be a function of time, but are nonlinear. For example, the wear duration adjustment can assume an exponential function with a pre-specified time constant and a pre-specified steady-state value. For example, f_gWear=G_wQ0+[G_wQ1*T_wear]+[G_wQ2*T_wear*T_wear], where G_wQ0, G_wQ1, and G_wQ2 are pre-determined quadratic polynomial parameters. In another example, f_gWear=G_wE1*exp(Tau_wE1*T_wear), where the time constant Tau_wE1 scales the wear duration T_wear for the exponential function, scaled by G_wE1. In another example, f_gWear=G_wP1*A_wP1^[Tau wP1*T_wear], where instead of an exponential function exp(x), a general power function with pre-determined base A_wP1 is used.

Example Embodiments With Multiple Parameters for Duration-Based Adjustment

In some example embodiments, the duration-based adjustment algorithms can be modified to provide greater flexibility to accommodate sensors of different configurations or chemistries. For example, different chemistry formulations may result in one sensor 101 (or sensor control device 102) requiring relatively greater shelf and/or wear duration adjustments than a second sensor 101 (or sensor control device 102), where the durations themselves are equal. In these embodiments, secondary adjustment parameters can be used as follows:

$$f\_gWear = K\_G0\_wear \times Y\_G0\_wear \times T\_wear \quad (9)$$

$$f\_sWear = R\_Sc\_wear \times Y\_Sc\_wear \times T\_wear \quad (10)$$

$$f\_gShelf = K\_G0\_shelf \times Y\_G0\_shelf \times T\_shelf \quad (11)$$

$$f\_sShelf = R\_Sc\_shelf \times Y\_Sc\_shelf \times T\_shelf \quad (12)$$

where Y_G0_wear is a secondary adjustment factor for wear duration for the G0 parameter, Y_Sc_wear is a secondary adjustment factor for wear duration for the G0 parameter, Y_G0_shelf is a secondary adjustment factor for shelf duration for the G0 parameter, and Y_Sc_shelf is a secondary adjustment factor for shelf duration for the Sc parameter.

The secondary adjustment parameters can scale the resulting adjustment functions to compensate for the different tendencies of the sensitivities of different sensor configurations to change over time. For example, one sensor control device 102 could have a multiplier Y_Sc_shelf as 0.8, while another set can take on a more aggressive multiplier Y_Sc_shelf as 2.3, such that when the shelf duration adjustment is applied, the second set of sensor control devices 102 will see more adjustment over the same shelf life duration Example Embodiments Incorporating One or More Additional Variables In other embodiments, the determination of sensor response change can utilize other information in addition to time. For example, all of the embodiments of shelf and/or wear duration adjustments described herein can be modified to account for incremental temperature exposure by utilizing an available temperature measurement yT for sensor control device 102. For example, with respect to wear duration:

$$f\_sWear = R\_Sc\_wear \times f\_sWearTemp(yT, T\_wear) \tag{13}$$

The function f_sWearTemp can compensate for temperature exposure, for example, using an integral as follows:

$$f\_sWearTemp(yT, T\_wear) = [1 - [A\_sW \exp(-E\_sW/zT)]]] \tag{14}$$

$$zT(\tau = T\_wear) = \frac{1}{T\_wear} \int_{\tau=0}^{\tau=T\_wear} yT(\tau)d\tau \tag{15}$$

where zT is the accumulated temperature related exposure based on the temperature measurement yT. The temperature measurement yT can be collected by sensor control device 102 with a temperature sensor that measures the ambient temperature of sensor control device 102 or the temperature of the user's body.

With respect to shelf duration adjustments, while sensor control device 102 is in storage, it can be configured to periodically power up in order to measure the ambient temperature (yT), which can then be stored in memory or used to update a cumulative temperature assessment (zT, below), so that a shelf duration adjustment similar to the aforementioned wear duration adjustment can be made:

$$f\_sShelf = R\_Sc\_shelf \times f\_sShelfTemp(yT, T\_shelf) \tag{16}$$

The function f_sShelfTemp can compensate for temperature exposure, for example, by estimating an integral exposure from the periodic sample in a zero-order-hold manner as follows:

$$f\_sShelfTemp(yT, T\_wear) = [1 - [A\_sS \exp(-E\_sS/zT)]]] \tag{17}$$

$$zT(\tau = T\_shelf) = \frac{1}{T\_shelf} \int_{\tau=0}^{\tau=T\_shelf} yT(\tau - \Delta\tau)\Delta\tau \tag{18}$$

where $\Delta\tau$ is the periodic interval of temperature measurement sampling. Those skilled in the art can determine the values A_sW, A_sS, E_sW, and E_sS from, e.g., a combination of first principles and empirical data.

In some embodiments, instead of using multiple discrete temperature measurements to estimate aggregated thermal exposure over time, a time temperature indicator (TTI) can be used to obtain a single estimated value for aggregate thermal exposure during storage. Examples of TTIs are described in "Time temperature indicators as devices intelligent packaging," Acta Universitatis Agriculturae et Silviculturae Mendelianae Brunensis, 2013, LXI, No. 1, pp. 245-251, and in U.S. Pat. No. 6,950,028 (titled "Electronic Time-Temperature Indicator"), both of which are incorporated by reference herein. For example, a TTI can be included with sensor control device 102 (e.g., as a form of temperature sensor 257, or on the packaging of sensor control device 102) and used to collect information indicative of the aggregate temperature (optionally over a predetermined limit) to which sensor 101 is exposed post-manufacture. In some embodiments, the output of the TTI can be read optically by a user, and then subsequently entered into the appropriate device of system 100 (e.g., sensor control device 102, reader 120, etc.), the processing circuitry of which can then use the entered information to perform a shelf duration adjustment to the analyte data. In other embodiments, the output of the TTI can be electronic and obtainable by the processing circuitry (e.g., of sensor control device 102) without intervention of the user and used to perform a shelf duration adjustment of the analyte data. In still other embodiments, the output of the TTI can be read over a wireless connection, e.g., by an RFID or NFC tag, and the user can obtain the measurement by scanning the TTI with a sensor control device 102 or reader device 120 having the appropriate wireless communication circuitry. In some embodiments, because the output of the TTI incorporates both time and temperature information, the shelf adjustment algorithm can use this information alone, without a separate time value input.

Example Embodiments of Parameter Coding

The various parameters described herein (e.g., STI, STS, K_G0_wear, R_Sc_wear, K_G0_shelf, R_Sc_shelf, Y_G0_wear, Y_Sc_wear, Y_G0_shelf, Y_Sc_shelf, G_w1, G_w2, any and all time values, time periods, temperature measurements, time temperature measurements, and so on) can be stored in the devices of system 100 in any desired format. In some embodiments, any and all of these parameters can be stored as their actual value (represented in digital format). In other embodiments, any and all of these parameters can be stored in a coded format. The coded format can be decoded by reference to a software algorithm or lookup table. In some embodiments, to conserve memory space, the parameters can be stored as one of a finite set of codes that can be decoded to a corresponding value. Each of the parameters can be nonzero values, or codes corresponding to nonzero values, such that the adjustment results in an actual change from the first analyte value (e.g., G_init) to the second analyte value (e.g., G_cal).

For example, the secondary adjustment factors (e.g., Y_G0_wear, Y_Sc_wear, Y_G0_shelf, Y_Sc_shelf) can be stored as one of a predetermined number of codes (e.g., 5 codes), each of which can be decoded as a particular value (e.g., where a 0 code is zero, a 1 code is 0.1, a 2 code is 0.5, a 3 code is 1, and a 4 code is 1.2). Such an arrangement can conserve memory space.

Any and all parameters can be stored as a single code, e.g., a calibration code, that can be decoded to translate each of the respective parameters to their respective values. In some embodiments, various parameters are stored as different codes, e.g., a first code for STI and STS, a second code for the primary adjustment parameters (e.g., K_G0_wear, R_Sc_wear, K_G0_shelf, R_Sc_shelf), a third code for the secondary adjustment parameters (e.g., Y_G0_wear, Y_Sc_wear, Y_G0_shelf, Y_Sc_shelf), a fourth code for the shelf start time, and so forth. Each of these codes can be stored in sensor control device 102 at the time of manufacture and used as needed by sensor control device 102 to process the data, or communicated to a different device (e.g., reader 120) for data processing.

In one embodiment, certain memory space reserved for the date of manufacture is used to store the adjustment factor. For example, the memory originally allocated to store the day of the month (of the date of manufacture) no longer stores the day of the month, but stores the adjustment factor(s) instead.

Example Methods of Adjustment

Figure 4A:
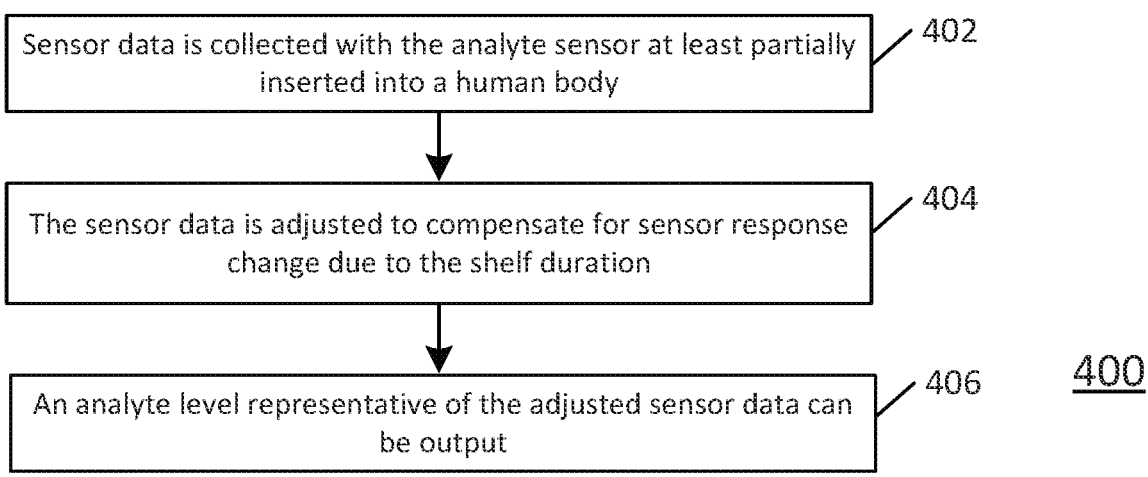
FIGS. 4A-4B are flow diagrams depicting example embodiments of methods for adjusting sensor data to compensate for shelf duration and wear duration, respectively.

Several example embodiments of methods of adjusting analyte sensor data are described with reference to FIGS. 4A-4B. FIG. 4A is a flow diagram depicting an example method 400 where sensor data is adjusted to compensate for a change in sensor response due to a shelf duration. At 402, sensor data is collected with the analyte sensor at least partially inserted into a human body. In some embodiments, a shelf duration of the analyte sensor can be determined with processing circuitry (e.g., of a sensor control device 102, a reader device 120, or other device of system 100). At 404, the sensor data is adjusted, with processing circuitry (e.g., of a sensor control device 102, a reader device 120, or other device of system 100), to compensate for the shelf duration. In some embodiments, the adjustment to the sensor data can be performed using the shelf duration (T_shelf) and one or more primary shelf duration adjustment parameters (e.g., K_G0_shelf, R_Sc_shelf), depending on the number of characteristics (e.g., slope, offset) being adjusted.

In some embodiments, temperature data representative of temperatures to which the analyte sensor was subjected during the shelf duration are collected, and then the sensor data is also adjusted to compensate for the temperature exposure during the shelf duration.

At 406, an analyte level representative of the adjusted sensor data can be output. Outputting of the adjusted sensor data can include, for example, communicating the adjusted sensor data from sensor control device 102 to a second electronic device (e.g., reader device 120) for further processing and/or display to a user, outputting the adjusted sensor data to the user directly from a display (e.g., of sensor control device 102 or reader device 120), or others.

Figure 4B:
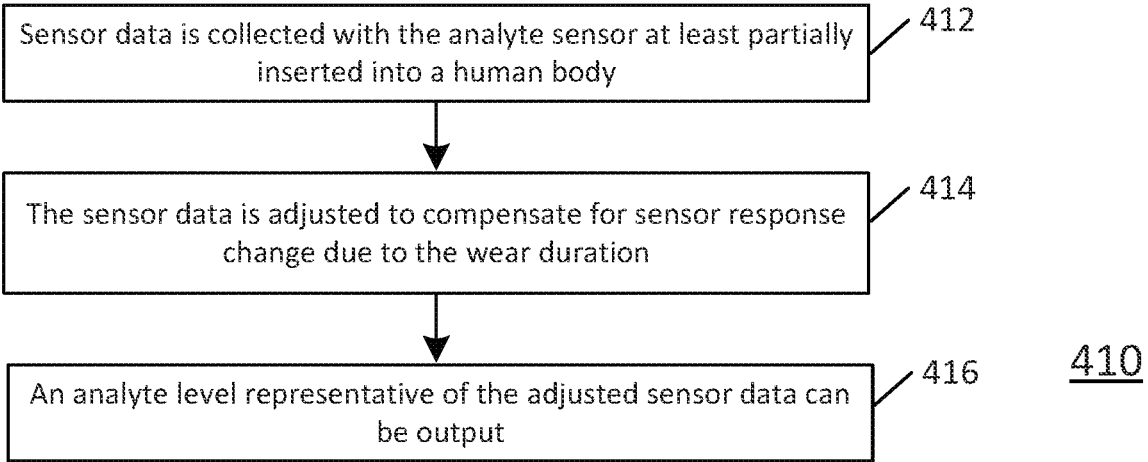

FIG. 4B is a flow diagram depicting an example method 410 where sensor data is adjusted to compensate for a change in sensor response due to a wear duration. At 412, sensor data is collected with the analyte sensor at least partially inserted into a human body. In some embodiments, a wear duration of the analyte sensor can be determined with processing circuitry (e.g., of a sensor control device 102, a reader device 120, or other device of system 100). At 414, the sensor data is adjusted, with processing circuitry (e.g., of a sensor control device 102, a reader device 120, or other device of system 100), to compensate for the wear duration. In some embodiments, the adjustment to the sensor data can be performed using the wear duration (T_wear) and one or more primary wear duration adjustment parameters (e.g., K_G0_wear, R_Sc_wear), depending on the number of characteristics (e.g., slope, offset) being adjusted.

In some embodiments, temperature data representative of temperatures to which the analyte sensor was subjected during the wear duration are collected, and then the sensor data is also adjusted to compensate for the temperature exposure during the wear duration.

At 416, an analyte level representative of the adjusted sensor data can be output. Outputting of the adjusted sensor data can include, for example, communicating the adjusted sensor data from sensor control device 102 to a second electronic device (e.g., reader device 120) for further processing and/or display to a user, outputting the adjusted sensor data to the user directly from a display (e.g., of sensor control device 102 or reader device 120), or others.

In another example embodiment, the collected sensor data is adjusting to compensate for sensor response changes for both shelf duration and wear duration.

The embodiments described herein are restated and expanded upon in the following paragraphs without explicit reference to the figures. In many embodiments, a method of adjusting analyte sensor data is provided, where the method includes: collecting sensor data with an analyte sensor at least partially inserted into a human body; adjusting, with processing circuitry, the sensor data to compensate for at least a first duration of time, where the first duration of time is one of a shelf duration or a wear duration; and outputting an analyte level representative of the adjusted sensor data. In many embodiments, the adjusted sensor data is different from the collected sensor data. In some embodiments, the analyte sensor is a glucose sensor.

In some embodiments, the method further includes adjusting, with processing circuitry, the sensor data to compensate for a first duration of time and a second duration of time, where the first duration of time is the shelf duration and the second duration of time is the wear duration.

In some embodiments, the first duration of time is the shelf duration, and the method further includes determining the shelf duration with processing circuitry. In some embodiments, the shelf duration can be representative of a period of time after the analyte sensor was manufactured and before the analyte sensor was inserted into the human body. In some embodiments, the shelf duration can include the entire time the analyte sensor was in a packaged state prior to insertion into the human body. In some embodiments, a wait period is implemented such that the shelf duration is representative of a time period less than the entire time the analyte sensor was in a packaged state prior to insertion.

In some embodiments, the analyte sensor has a sensitivity at least partially represented by a slope and/or an intercept, and the step of adjusting, with processing circuitry, the sensor data to compensate for the shelf duration includes adjusting at least one of the slope and the intercept.

In some embodiments, the method further includes collecting temperature data representative of a plurality of temperatures to which the analyte sensor was subjected during the shelf duration. In some embodiments, the method further includes adjusting, with processing circuitry, the sensor data to compensate for the shelf duration and the plurality of temperatures.

In some embodiments, the first duration of time is the wear duration, the method further including determining the wear duration with processing circuitry. In some embodiments, the wear duration is representative of a period of time during which the analyte sensor is at least partially inserted into the human body. In some embodiments, the wear duration begins upon insertion of the analyte sensor into the human body. In some embodiments, a wait period is implemented such that the wear duration begins a period of time period after insertion of the analyte sensor into the human body. In some embodiments, a sensor control device includes the analyte sensor and sensor electronics, and the wear duration begins upon activation of the sensor control device.

In some embodiments, the analyte sensor has a sensitivity at least partially represented by a slope and/or an intercept, and the step of adjusting, with processing circuitry, the sensor data to compensate for the wear duration includes adjusting the slope, the intercept, or both.

In some embodiments, the method further includes collecting temperature data representative of a plurality of temperatures to which the analyte sensor was subjected during the wear duration. In some embodiments, the method further includes adjusting, with processing circuitry, the sensor data to compensate for the wear duration and the plurality of temperatures.

In some embodiments, adjusting, with processing circuitry, the sensor data to compensate for the shelf duration includes: adjusting, with processing circuitry, the sensor data with a function including an adjustment parameter and a value representative of time. In some embodiments, the adjustment parameter corresponds to a code selected from one of a plurality of codes, and the method further includes: decoding, with processing circuitry, the code to determine the adjustment parameter. In some embodiments, the adjustment parameter corresponds to a code selected from one of a plurality of codes, and the method further includes: communicating the code from a sensor control device to a reader device; decoding, with processing circuitry of the reader device, the code to determine the adjustment parameter; and adjusting, with processing circuitry of the reader device, the sensor data with the function including the adjustment parameter and the value representative of time. In some embodiments, the value representative of time is representative of a shelf duration. In some embodiments, the value representative of time is representative of a shelf duration less a wait period. In some embodiments, the adjustment factor is stored in memory in an unencoded form, and the method further includes: adjusting, with processing circuitry, the sensor data without decoding the adjustment factor.

In some embodiments, adjusting, with processing circuitry, the sensor data to compensate for the wear duration includes: adjusting, with processing circuitry, the sensor data with a function including an adjustment parameter and a value representative of time. In some embodiments, the adjustment parameter corresponds to a code selected from one of a plurality of codes, the method further including: decoding, with processing circuitry, the code to determine the adjustment parameter. In some embodiments, the adjustment parameter corresponds to a code selected from one of a plurality of codes, the method further including: communicating the code from a sensor control device to a reader device; decoding, with processing circuitry of the reader device, the code to determine the adjustment parameter; and adjusting, with processing circuitry of the reader device, the sensor data with the function including the adjustment parameter and the value representative of time. In some embodiments, the value representative of time is representative of a wear duration. In some embodiments, the value representative of time is representative of a wear duration less a wait period. In some embodiments, the adjustment factor is stored in memory in an unencoded form, the method further including: adjusting, with processing circuitry, the sensor data without decoding the adjustment factor.

In many embodiments, an analyte monitoring system is provided, the analyte monitoring system including: a sensor control device including an analyte sensor at least partially insertable into a human body, processing circuitry, and a non-transitory memory, where the sensor control device is configured to collect sensor data with the analyte sensor; and a reader device including processing circuitry and a non-transitory memory, where at least one of the non-transitory memories of the sensor control device or reader device includes instructions that, when executed, cause at least one of the processing circuitries of the sensor control device or the reader device to: adjust collected sensor data to compensate for at least a first duration of time, where the first duration of time is one of a shelf duration or a wear duration; and cause output of an analyte level representative of the adjusted sensor data. In many embodiments, the adjusted sensor data is different from the collected sensor data. In some embodiments, the analyte sensor is a glucose sensor.

In some embodiments, at least one of the non-transitory memories of the sensor control device or reader device includes instructions that, when executed, cause at least one of the processing circuitries of the sensor control device or the reader device to: adjust the collected sensor data to compensate for a first duration of time and a second duration of time, where the first duration of time is the shelf duration and the second duration of time is the wear duration.

In some embodiments, the first duration of time is the shelf duration, and where at least one of the non-transitory memories of the sensor control device or reader device includes instructions that, when executed, cause at least one of the processing circuitries of the sensor control device or the reader device to: determine the shelf duration.

In some embodiments, at least one of the non-transitory memories of the sensor control device or reader device includes instructions that, when executed, cause at least one of the processing circuitries of the sensor control device or the reader device to: determine the shelf duration such that the shelf duration is representative of a period of time after the analyte sensor was manufactured and before the analyte sensor was inserted into the human body. In some embodiments, at least one of the non-transitory memories of the sensor control device or reader device includes instructions that, when executed, cause at least one of the processing circuitries of the sensor control device or the reader device to: determine the shelf duration such that the shelf duration includes the entire time the analyte sensor was in a packaged state prior to insertion into the human body. In some embodiments, at least one of the non-transitory memories of the sensor control device or reader device includes instructions that, when executed, cause at least one of the processing circuitries of the sensor control device or the reader device to: determine the shelf duration such that it begins after a post-manufacture wait period.

In some embodiments, the sensor control device is programmed to communicate an adjustment parameter to the reader device, the adjustment parameter being representative of a nonzero value and usable with a shelf duration time value to compensate for shelf duration.

In some embodiments, the analyte sensor has a sensitivity at least partially represented by a slope and/or an intercept, and where at least one of the non-transitory memories of the sensor control device or reader device includes instructions that, when executed, cause at least one of the processing circuitries of the sensor control device or the reader device to: adjust at least one of the slope, the intercept, or both to compensate for the shelf duration.

In some embodiments, the sensor control device further includes a temperature sensor adapted to collect temperature data representative of a plurality of temperatures to which the analyte sensor is subjected during the shelf duration. In some embodiments, at least one of the non-transitory memories of the sensor control device or reader device includes instructions that, when executed, cause at least one of the processing circuitries of the sensor control device or the reader device to: adjust the sensor data to compensate for the shelf duration and the plurality of temperatures.

In some embodiments, the first duration of time is the wear duration, and at least one of the non-transitory memories of the sensor control device or reader device includes instructions that, when executed, cause at least one of the processing circuitries of the sensor control device or the reader device to: determine the wear duration. In some embodiments, at least one of the non-transitory memories of the sensor control device or reader device includes instructions that, when executed, cause at least one of the processing circuitries of the sensor control device or the reader device to: determine the wear duration such that the wear duration is representative of a period of time during which the analyte sensor is at least partially inserted into the human body. In some embodiments, at least one of the non-transitory memories of the sensor control device or reader device includes instructions that, when executed, cause at least one of the processing circuitries of the sensor control device or the reader device to: determine the wear duration from the time of insertion of the analyte sensor into the human body. In some embodiments, a sensor control device includes the analyte sensor and sensor electronics, and at least one of the non-transitory memories of the sensor control device or reader device includes instructions that, when executed, cause at least one of the processing circuitries of the sensor control device or the reader device to: determine the wear duration from the time of activation of the sensor control device. In some embodiments, at least one of the non-transitory memories of the sensor control device or reader device includes instructions that, when executed, cause at least one of the processing circuitries of the sensor control device or the reader device to: determine the wear duration such that it begins after a post-insertion wait period.

In some embodiments, the sensor control device is programmed to communicate an adjustment parameter to the reader device, the adjustment parameter being representative of a nonzero value and usable with a wear duration time value to compensate for wear duration.

In some embodiments, the analyte sensor has a sensitivity at least partially represented by a slope and/or an intercept, and where at least one of the non-transitory memories of the sensor control device or reader device includes instructions that, when executed, cause at least one of the processing circuitries of the sensor control device or the reader device to: adjust at least one of the slope, the intercept, or both to compensate for the wear duration.

In some embodiments, the sensor control device further includes a temperature sensor adapted to collect temperature data representative of a plurality of temperatures to which the analyte sensor is subjected during the wear duration. In some embodiments, at least one of the non-transitory memories of the sensor control device or reader device includes instructions that, when executed, cause at least one of the processing circuitries of the sensor control device or the reader device to: adjust the sensor data to compensate for the wear duration and the plurality of temperatures.

In some embodiments, the non-transitory memory of the sensor control device includes instructions that, when executed, cause the processing circuitry of the sensor control device to: adjust collected sensor data to compensate for at least a first duration of time, where the first duration of time is one of a shelf duration or a wear duration; and cause output an analyte level representative of the adjusted sensor data to the reader device or to a user.

In some embodiments, the non-transitory memory of the reader device includes instructions that, when executed, cause the processing circuitry of the reader device to: adjust collected sensor data to compensate for at least a first duration of time, where the first duration of time is one of a shelf duration or a wear duration; and cause output an analyte level representative of the adjusted sensor data.

In some embodiments, at least one of the non-transitory memories of the sensor control device or reader device includes instructions that, when executed, cause at least one of the processing circuitries of the sensor control device or the reader device to: adjust the sensor data, to compensate for shelf duration, with a function including an adjustment parameter and a value representative of time. In some embodiments, the adjustment parameter corresponds to a code selected from one of a plurality of codes, and where at least one of the non-transitory memories of the sensor control device or reader device includes instructions that, when executed, cause at least one of the processing circuitries of the sensor control device or the reader device to: decode the code to determine the adjustment parameter. In some embodiments, the adjustment parameter corresponds to a code selected from one of a plurality of codes, and where the sensor control device is programmed to communicate the code to the reader device. In some embodiments, the non-transitory memory of the reader device includes instructions that, when executed, causes the processing circuitry of the reader device to: decode the code to determine the adjustment parameter; and adjust the sensor data with the function including the adjustment parameter and the value representative of time. In some embodiments, the value representative of time is representative of a shelf duration. In some embodiments, the value representative of time is representative of a shelf duration less a wait period. In some embodiments, the adjustment factor is stored in the non-transitory memory of the sensor control device in an unencoded form, and where the sensor control device is programmed to communicate the unencoded adjustment factor to the reader device.

In some embodiments, at least one of the non-transitory memories of the sensor control device or reader device includes instructions that, when executed, cause at least one of the processing circuitries of the sensor control device or the reader device to: adjust the sensor data, to compensate for wear duration, with a function including an adjustment parameter and a value representative of time. In some embodiments, the adjustment parameter corresponds to a code selected from one of a plurality of codes, and where at least one of the non-transitory memories of the sensor control device or reader device includes instructions that, when executed, cause at least one of the processing circuitries of the sensor control device or the reader device to: decode the code to determine the adjustment parameter. In some embodiments, the adjustment parameter corresponds to a code selected from one of a plurality of codes, and where the sensor control device is programmed to communicate the code to the reader device. In some embodiments, the non-transitory memory of the reader device includes instructions that, when executed, causes the processing circuitry of the reader device to: decode the code to determine the adjustment parameter; and adjust the sensor data with the function including the adjustment parameter and the value representative of time. In some embodiments, the value representative of time is representative of a wear duration. In some embodiments, the value representative of
time is representative of a wear duration less a wait period.
In some embodiments, the adjustment factor is stored in the
non-transitory memory of the sensor control device in an
unencoded form, and where the sensor control device is
programmed to communicate the unencoded adjustment
factor to the reader device.

For each and every embodiment of a method disclosed
herein, systems and devices capable of performing each of
those embodiments are covered within the scope of the
present disclosure. For example, embodiments of sensor
control devices are disclosed, and these devices can have
one or more analyte sensors, analyte monitoring circuits
(e.g., an analog circuit), memories (e.g., for storing instruc-
tions), power sources, communication circuits, transmitters,
receivers, clocks, counters, times, temperature sensors, pro-
cessors (e.g., for executing instructions) that can perform
any and all method steps or facilitate the execution of any
and all method steps. These sensor control device embodi-
ments can be used and can be capable of use to implement
those steps performed by a sensor control device from any
and all of the methods described herein. Similarly, embodi-
ments of reader devices are disclosed, and these devices can
have one or more memories (e.g., for storing instructions),
power sources, communication circuits, transmitters, receivers, clocks, counters, times, and processors (e.g., for execut-
ing instructions) that can perform any and all method steps
or facilitate the execution of any and all method steps. These
reader device embodiments can be used and can be capable
of use to implement those steps performed by a reader
device from any and all of the methods described herein.
Embodiments of computer devices and servers are dis-
closed, and these devices can have one or more memories
(e.g., for storing instructions), power sources, communica-
tion circuits, transmitters, receivers, clocks, counters, times,
and processors (e.g., for executing instructions) that can
perform any and all method steps or facilitate the execution
of any and all method steps. These reader device embodi-
ments can be used and can be capable of use to implement
those steps performed by a reader device from any and all of
the methods described herein.

Computer program instructions for carrying out opera-
tions in accordance with the described subject matter may be
written in any combination of one or more programming
languages, including an object oriented programming language such as Java, JavaScript, Smalltalk, C++, C#, Trans-
act-SQL, XML, PHP or the like and conventional procedural
programming languages, such as the "C" programming
language or similar programming languages. The program
instructions may execute entirely on the user's computing
device, partly on the user's computing device, as a stand-
alone software package, partly on the user's computing
device and partly on a remote computing device or entirely
on the remote computing device or server. In the latter
scenario, the remote computing device may be connected to
the user's computing device through any type of network,
including a local area network (LAN) or a wide area network
(WAN), or the connection may be made to an external
computer (for example, through the Internet using an Inter-
net Service Provider).

It should be noted that all features, elements, components,
functions, and steps described with respect to any embodi-
ment provided herein are intended to be freely combinable
and substitutable with those from any other embodiment. If
a certain feature, element, component, function, or step is
described with respect to only one embodiment, then it
should be understood that that feature, element, component, function, or step can be used with every other embodiment
described herein unless explicitly stated otherwise. This
paragraph therefore serves as antecedent basis and written
support for the introduction of claims, at any time, that
combine features, elements, components, functions, and
steps from different embodiments, or that substitute features,
elements, components, functions, and steps from one
embodiment with those of another, even if the following
description does not explicitly state, in a particular instance,
that such combinations or substitutions are possible. It is
explicitly acknowledged that express recitation of every
possible combination and substitution is overly burdensome,
especially given that the permissibility of each and every
such combination and substitution will be readily recognized
by those of ordinary skill in the art.

To the extent the embodiments disclosed herein include or
operate in association with memory, storage, and/or com-
puter readable media, then that memory, storage, and/or
computer readable media are non-transitory. Accordingly, to
the extent that memory, storage, and/or computer readable
media are covered by one or more claims, then that memory,
storage, and/or computer readable media is only non-tran-
sitory.

As used herein and in the appended claims, the singular
forms "a," "an," and "the" include plural referents unless the
context clearly dictates otherwise.

While the embodiments are susceptible to various modi-
fications and alternative forms, specific examples thereof
have been shown in the drawings and are herein described
in detail. It should be understood, however, that these
embodiments are not to be limited to the particular form
disclosed, but to the contrary, these embodiments are to
cover all modifications, equivalents, and alternatives falling
within the spirit of the disclosure. Furthermore, any features,
functions, steps, or elements of the embodiments may be
recited in or added to the claims, as well as negative
limitations that define the inventive scope of the claims by
features, functions, steps, or elements that are not within that
scope.

What is claimed is:

1. A glucose monitoring sensor control device compris-
ing:
a glucose sensor configured to detect glucose levels in a
bodily fluid of a user, wherein the glucose sensor is
configured to be positioned in the user such that when
operably positioned, a first portion of the glucose
sensor is configured to reside above a skin surface of
the user, and a second portion of the glucose sensor is
configured to reside below the skin surface and in
contact with the bodily fluid of the user;
processing circuitry electrically and communicatively
coupled with the glucose sensor prior to the glucose
sensor being positioned in the user; and
a memory electrically and communicatively coupled with
the processing circuitry, the memory comprising
instructions that, when executed by the processing
circuitry, cause the processing circuitry to:
collect data indicative of environmental exposure of the
glucose sensor during a duration of time before use
of the sensor control device by the user;
determine a wear duration of the glucose sensor,
wherein the wear duration corresponds to a duration
of time after use of the sensor control device by the
user;
collect, from the glucose sensor, sensor data including
data indicative of a glucose level in the bodily fluid;

algorithmically adjust a calibration parameter of the glucose sensor with: a first function including a first adjustment parameter and a value representative of the wear duration, and one or more additional functions including a second adjustment parameter and a value representative of the environmental exposure of the glucose sensor during the duration of time before use of the sensor control device by the user;

algorithmically process the sensor data using the adjusted calibration parameter and to determine the glucose level in the bodily fluid; and transmit the determined glucose level to a reader device communicatively coupled with the sensor control device and configured to display the determined glucose level.

2. The glucose monitoring sensor control device of claim 1, wherein the first function including the first adjustment parameter and the value representative of the wear duration comprises a first adjustment function for values of the value representative of the wear duration below a threshold value and a second adjustment function for values of the value representative of the wear duration above the threshold value.

3. The glucose monitoring sensor control device of claim 1, wherein the first adjustment parameter and second adjustment parameter are pre-determined and provided to the memory prior to the use of the sensor control device by the user.

4. The glucose monitoring sensor control device of claim 1, wherein the first adjustment parameter and second adjustment parameter are pre-determined in manufacture of the glucose sensor.

5. The glucose monitoring sensor control device of claim 1, wherein the instructions to determine the wear duration further cause the processing circuitry to calculate a difference between a supplied present time and a wear start time corresponding to a beginning of the duration of time after use of the sensor control device by the user.

6. The glucose monitoring sensor control device of claim 1, wherein the instructions to determine the wear duration further cause the processing circuitry to incorporate a wait period to the wear duration such that the wear duration corresponds to a duration of time less than the entire time after the use of the sensor control device by the user.

7. The glucose monitoring sensor control device of claim 1, wherein the memory further comprises instructions that, when executed by the processing circuitry cause the processing circuitry to:

detect that the glucose sensor has been positioned in the user, wherein the use of the sensor control device by the user corresponds to the detection that the glucose sensor has been positioned in the user.

8. The glucose monitoring sensor control device of claim 1, wherein the memory further comprises instructions that, when executed by the processing circuitry cause the processing circuitry to:

receive an electrical signal from the glucose sensor; and detect the use of the sensor control device by the user based on receiving the electrical signal.

9. The glucose monitoring sensor control device of claim 1, wherein the use of the sensor control device by the user comprises activation of the sensor control device by an insertion device configured to position the second portion of the glucose sensor below the skin surface and in contact with the bodily fluid of the user.

10. The glucose monitoring sensor control device of claim 1, wherein the memory further comprises instructions that, when executed by the processing circuitry cause the processing circuitry to:

determine a shelf duration of the glucose sensor corresponding to the duration of time before use of the sensor control device by the user; and algorithmically adjust the calibration parameter of the glucose sensor further with a third function including a third adjustment parameter and a value representative of the shelf duration.

11. The glucose monitoring sensor control device of claim 10, wherein the shelf duration corresponds to a duration of time after the glucose sensor has completed manufacturing.

12. The glucose monitoring sensor control device of claim 10, wherein the shelf duration corresponds to a duration of time after the glucose sensor has completed testing.

13. The glucose monitoring sensor control device of claim 10, wherein the shelf duration corresponds to a duration of time after the glucose sensor has completed assembly into the sensor control device.

14. The glucose monitoring sensor control device of claim 10, wherein the shelf duration corresponds to a duration of time after the glucose sensor has completed packaging.

15. The glucose monitoring sensor control device of claim 1, wherein the wear duration further corresponds to a duration of time after sensor data is first collected from the glucose sensor.

16. The glucose monitoring sensor control device of claim 1, wherein the wear duration further corresponds to a duration of time after the glucose level is first transmitted to the reader device.

17. The glucose monitoring sensor control device of claim 1, wherein:

the data indicative of the environmental exposure of the glucose sensor comprises temperature data representative of a plurality of temperatures to which the glucose sensor was subjected during the duration of time before use of the sensor control device by the user; and the value representative of the environmental exposure of the glucose sensor comprises a value representative of the plurality of temperatures.

18. The glucose monitoring sensor control device of claim 1, wherein:

the data indicative of the environmental exposure of the glucose sensor comprises an aggregate temperature data value representative of aggregated thermal exposure of the glucose sensor during the duration of time before use of the sensor control device by the user; and the value representative of the environmental exposure of the glucose sensor comprises a value representative of the aggregate temperature data.

19. The glucose monitoring sensor control device of claim 1, wherein the data indicative of the environmental exposure of the glucose sensor is indicative of exposure of the glucose sensor to humidity during the duration of time before use of the sensor control device by the user.

20. The glucose monitoring sensor control device of claim 1, wherein the data indicative of the environmental exposure of the glucose sensor is indicative of exposure of the glucose sensor to air pressure during the duration of time before use of the sensor control device by the user.

21. The glucose monitoring sensor control device of claim 20, wherein the sensitivity parameter is an offset of the linear sensitivity.

22. The glucose monitoring sensor control device of claim 20, wherein the sensitivity parameter is a slope of the linear sensitivity.

23. The glucose monitoring sensor control device of claim 1, wherein the calibration parameter comprises a sensitivity parameter for a linear sensitivity of the glucose sensor.

24. A method of algorithmically processing glucose sensor data, comprising:

collecting data indicative of environmental exposure of a glucose sensor during a duration of time before use of the sensor control device by the user, wherein the glucose sensor is configured to detect glucose levels in a bodily fluid of a user such that a first portion of the glucose sensor is configured to reside above a skin surface of the user and a second portion of the glucose sensor is configured to reside below the skin surface and in contact with the bodily fluid of the user;

retrieving the data indicative of environmental exposure of the glucose sensor during the duration of time before use of the sensor control device by the user;

determining a wear duration of the glucose sensor, wherein the wear duration corresponds to a duration of time after use of the sensor control device by the user;

collecting, from the glucose sensor, sensor data including data indicative of a glucose level in the bodily fluid while the glucose sensor is in a position with the first portion of the glucose sensor above the skin surface of the user and the second portion of the glucose sensor below the skin surface and in contact with the bodily fluid of the user, the glucose sensor having been placed in the position with an insertion device, wherein the glucose sensor was electrically and communicatively coupled with processing circuitry of the sensor control device prior to placement of the glucose sensor in the position;

algorithmically adjusting a calibration parameter of the glucose sensor with: a first function including a first adjustment parameter and a value representative of the wear duration, and one or more additional functions including a second adjustment parameter and a value representative of the environmental exposure of the glucose sensor during the duration of time before use of the sensor control device by the user;

algorithmically processing the sensor data using the adjusted calibration parameter and to determine the glucose level in the bodily fluid; and transmitting the determined glucose level to a reader device communicatively coupled with the sensor control device and configured to display the determined glucose level.

25. The method of claim 24, further comprising activating the sensor control device using the insertion device.

26. An analyte monitoring system, comprising:

a glucose monitoring sensor control device comprising:

an adhesive patch configured to couple the glucose monitoring sensor control device to a skin surface of a user;

a glucose sensor configured to detect glucose levels in a bodily fluid of the user, wherein the glucose sensor is configured to be positioned in the user such that when operably positioned, a first portion of the glucose sensor is configured to reside above the skin surface of the user, and a second portion of the glucose sensor is configured to reside below the skin surface and in contact with the bodily fluid of the user;

an antenna;

sensor electronics and a power source coupled with the sensor electronics, wherein the sensor electronics comprise:

analog front end circuitry configured to interface with the glucose sensor and receive measurement data therefrom;

communication circuitry configured for wireless communication with a reader device by way of the antenna;

processing circuitry electrically and communicatively coupled with the analog front end circuitry and glucose sensor prior to the glucose sensor being positioned in the user; and a memory electrically and communicatively coupled with the processing circuitry, the memory comprising instructions that, when executed by the processing circuitry, cause the processing circuitry to:

collect data indicative of environmental exposure of the glucose sensor during a duration of time before use of the sensor control device by the user;

determine a wear duration of the glucose sensor, wherein the wear duration corresponds to a duration of time after use of the sensor control device by the user;

collect, from the glucose sensor, sensor data including data indicative of a glucose level in the bodily fluid;

algorithmically adjust a calibration parameter of the glucose sensor with: a first function including a first adjustment parameter and a value representative of the wear duration, and one or more additional functions including a second adjustment parameter and a value representative of the environmental exposure of the glucose sensor during the duration of time before use of the sensor control device by the user;

algorithmically process the sensor data using the adjusted calibration parameter and to determine the glucose level in the bodily fluid; and transmit the determined glucose level to a reader device communicatively coupled with the sensor control device and configured to display the determined glucose level, and an insertion device configured to position the glucose monitoring sensor control device and the adhesive patch onto the skin surface of the user and to position the second portion of the glucose sensor below the skin surface and in contact with the bodily fluid of the user.

27. The analyte monitoring system of claim 26, wherein:

the data indicative of the environmental exposure of the glucose sensor comprises temperature data representative of a plurality of temperatures to which the glucose sensor was subjected during the duration of time before use of the sensor control device by the user; and the value representative of the environmental exposure of the glucose sensor comprises a value representative of the plurality of temperatures.

28. The analyte monitoring system of claim 26, wherein the data indicative of the environmental exposure of the glucose sensor is indicative of exposure of the glucose sensor to humidity during the duration of time before use of the sensor control device by the user.

* * * * *